US011751770B2

(12) United States Patent
Brown et al.

(10) Patent No.: US 11,751,770 B2
(45) Date of Patent: Sep. 12, 2023

(54) SYSTEM AND METHOD FOR TRACKING BRAIN STATES DURING ADMINISTRATION OF ANESTHESIA

(71) Applicant: The General Hospital Corporation, Boston, MA (US)

(72) Inventors: Emery N. Brown, Brookline, MA (US); Patrick L. Purdon, Boston, MA (US); Aylin Cimenser, Cambridge, MA (US); Eran A. Mukamel, La Jolla, CA (US); Michael J. Prerau, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 1167 days.

(21) Appl. No.: 16/165,580

(22) Filed: Oct. 19, 2018

(65) Prior Publication Data

US 2019/0117085 A1  Apr. 25, 2019

Related U.S. Application Data

(63) Continuation of application No. 14/115,682, filed as application No. PCT/US2012/036854 on May 7, 2012, now abandoned.

(Continued)

(51) Int. Cl.
*A61B 5/00* (2006.01)
*A61B 5/0205* (2006.01)
(Continued)

(52) U.S. Cl.
CPC ............ *A61B 5/0205* (2013.01); *A61B 5/369* (2021.01); *A61B 5/374* (2021.01); *A61B 5/4821* (2013.01);
(Continued)

(58) Field of Classification Search
None
See application file for complete search history.

(56) References Cited

U.S. PATENT DOCUMENTS 6,016,444 A   1/2000  John
6,067,467 A   5/2000  John
(Continued)

FOREIGN PATENT DOCUMENTS

| JP | 2008178546 A | 8/2008 |
|---|---|---|
| RU | 95243 U1 | 6/2010 |
| WO | 2004037114 A2 | 5/2004 |

OTHER PUBLICATIONS

Molaee-Ardekani et al. Delta waves differently modulate high frequency components of EEG oscillations ion various unconsciousness levels, 2007, Proceedings of the 29th Annual International Conference of the IEE EMBS, 1294-1297 (Year: 2007).*

(Continued)

*Primary Examiner* — Michael R Bloch
(74) *Attorney, Agent, or Firm* — QUARLES & BRADY LLP

(57) ABSTRACT

A method and system for determining the state of a patients brain under anesthesia. The present invention recognizes that anesthesia compounds induce different signatures in physiological characteristics of the patient under anesthesia and aids interpretation of physiological characteristics and signatures therein based on a selected anesthesia compound. The present invention aids the monitoring and/or interpreting of the physiological characteristics to a state of the patient's brain.

19 Claims, 16 Drawing Sheets

Related U.S. Application Data

(60) Provisional application No. 61/483,483, filed on May 6, 2011.

(51) Int. Cl.
*G16H 50/70* (2018.01)
*G16H 50/20* (2018.01)
*G06F 17/18* (2006.01)
*A61B 5/369* (2021.01)
*A61B 5/374* (2021.01)
*A61B 5/02* (2006.01)
*A61B 5/38* (2021.01)

(52) U.S. Cl.
CPC ............ *A61B 5/7246* (2013.01); *G06F 17/18* (2013.01); *G16H 50/20* (2018.01); *G16H 50/70* (2018.01); *A61B 5/02* (2013.01); *A61B 5/38* (2021.01); *A61B 5/7264* (2013.01); *G06F 2218/00* (2023.01)

(56) References Cited

U.S. PATENT DOCUMENTS

| | | | |
|---|---|---|---|
| 6,631,291 B2 | 10/2003 | Viertio-Oja et al. | |
| 2004/0193068 A1* | 9/2004 | Burton | A61B 5/4812 600/544 |
| 2006/0009733 A1 | 1/2006 | Martin | |
| 2007/0060831 A1* | 3/2007 | Le | A61B 5/7264 600/544 |
| 2008/0021345 A1 | 1/2008 | Kern et al. | |
| 2011/0015538 A1 | 1/2011 | Matthews, Jr. | |
| 2011/0118620 A1* | 5/2011 | Scheib | A61B 5/374 600/544 |
| 2011/0119212 A1 | 5/2011 | De Bruin et al. | |
| 2011/0295096 A1* | 12/2011 | Bibian | A61B 5/7221 600/372 |

OTHER PUBLICATIONS

Ching et al., Thalamocortical Model for a Propofol-Induced α-rhythm Associated with Loss of Consciousness, Proceedings of the National Academy of Sciences, 2010, 107(52):22665-22670.

Cimenser et al., Developing New Neurophysiological Signatures of General Anesthesia Induced Loss of Consciousness, BMC Neuroscience, 2009, 10(1):P79, 2 pages.

Cimenser et al., Tracking Brain States Under General Anesthesia by Using Global Coherence Analysis, Proceedings of the National Academy of Sciences, 2011, 108(21):8832-8837.

John et al., Invariant Reversible QEEG Effects of Anesthetics, Consciousness and Cognition, 2001, 10(2):165-183.

Mitra et al., Chapter 7—Time Series Analysis, In "Observed Brain Dynamics", Oxford University Press, UK, 2007, pp. 184-216.

Molaee-Ardekani et al., Delta Waves Differently Modulate High Frequency Components of EEG Oscillations in Various Unconsciousness Levels, In 2007 29th Annual International Conference of the IEEE Engineering in Medicine and Biology Society, pp. 1294-1297.

Mukamel et al., Phase-Based Measures of Cross-Frequency Coupling in Brain Electrical Dynamics Under General Anesthesia, In 2011 Annual International Conference of the IEEE Engineering in Medicine and Biology Society, pp. 1981-1984.

Smith et al., Bayesian Analysis of Interleaved Learning and Response Bias in Behavioral Experiments, Journal of Neurophysiology, 2007, 97(3):2516-2524.

Wong et al., Robust Time-Varying Multivariate Coherence Estimation: Application to Electroencephalogram Recordings During General Anesthesia, In 2011 Annual International Conference of the IEEE Engineering in Medicine and Biology Society, pp. 4725-4728.

Wong et al., Bayesian Analysis of Trinomial Data in Behavioral Experiments and Its Application to Human Studies of General Anesthesia, In 2011 Annual International Conference of the IEEE Engineering in Medicine and Biology Society, pp. 4705-4708.

PCT International Search Report and Written Opinion, PCT/US2012/036854, dated Aug. 16, 2012, 6 pages.

Lotte et al., A Review of Classification Algorithms for EEG-Based Brain-Computer Interfaces, Journal of Neural Engineering, 2007, vol. 4, 24 pages.

European Patent Office, Communication, Application No. 12781958.9, dated Sep. 27, 2021, 6 pages.

* cited by examiner

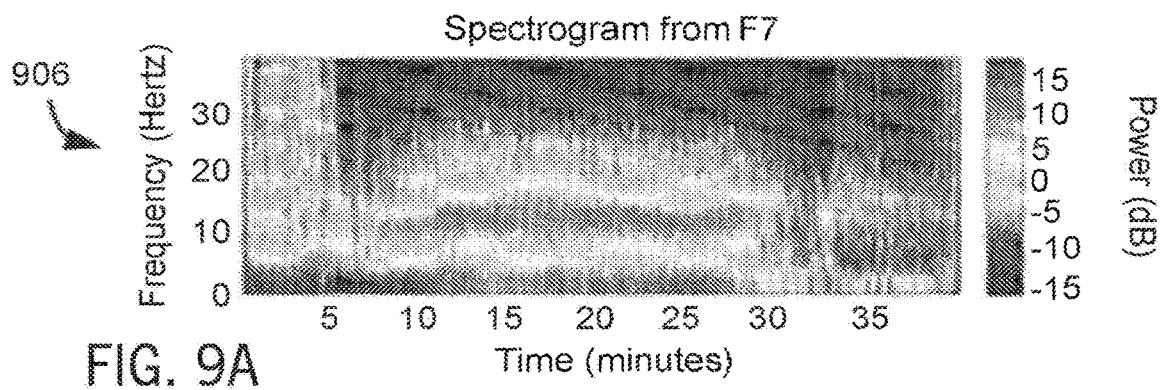
FIG. 9A
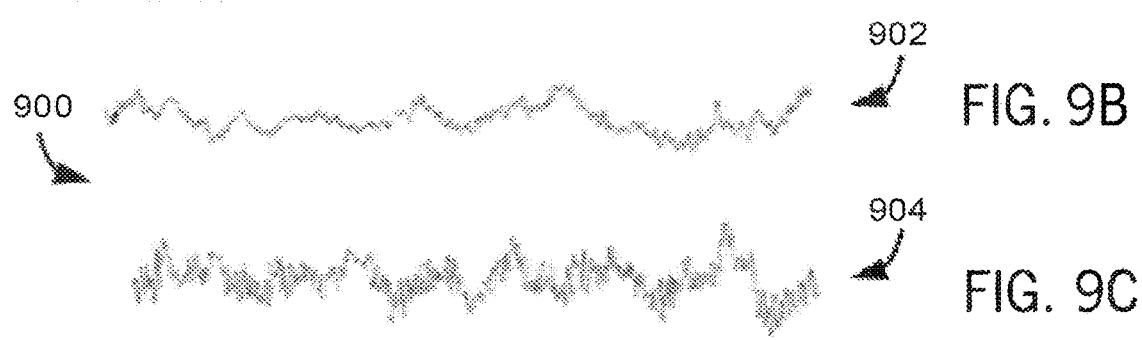
FIG. 9B
FIG. 9C
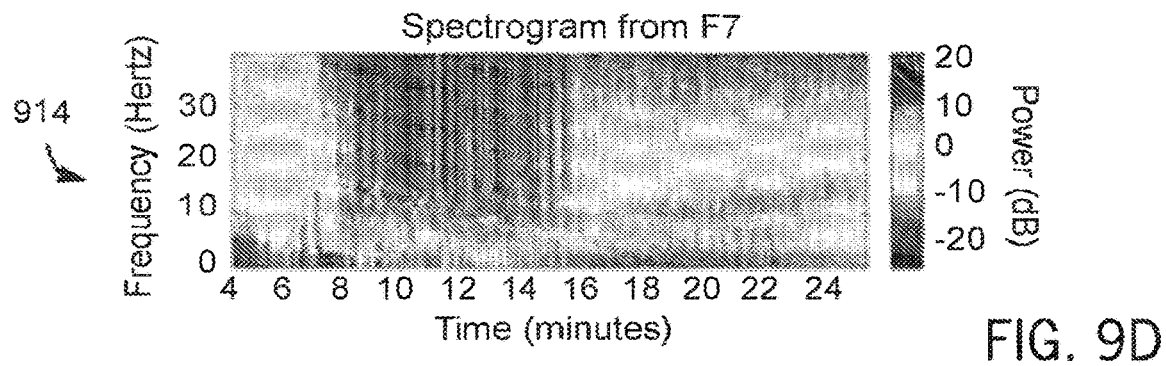
FIG. 9D
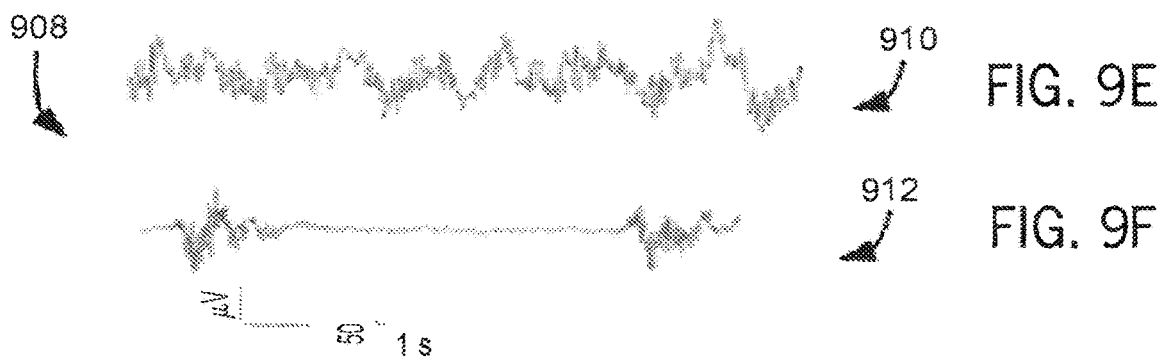
FIG. 9E
FIG. 9F

SYSTEM AND METHOD FOR TRACKING BRAIN STATES DURING ADMINISTRATION OF ANESTHESIA

CROSS-REFERENCE TO RELATED APPLICATIONS

This application is a continuation of U.S. application Ser. No. 14/115,682 filed Feb. 19, 2014 which represents the U.S. National Stage of International Application No. PCT/US2012/036854, filed May 7, 2012 which is based on, claims the benefit of, and incorporates herein by reference U.S. Provisional Application Ser. No. 61/483,483, filed May 6, 2011, and entitled, "A Method of Using EEG and Advanced Signal Processing Algorithms to Track Brain States Under General Anesthesia."

STATEMENT REGARDING FEDERALLY SPONSORED RESEARCH

This invention was made with government support under DP1 OD003646, DP2-OD006454, and K25-NS05758 awarded by the National Institutes of Health. The government has certain rights in the invention.

BACKGROUND OF THE INVENTION

The present invention relates to systems and methods for tracking brain states of a patient under anesthesia and, more particularly, to systems and methods for correlating anticipated effects of a given anesthetic compound administered to a patient with characteristics of the patient's brain state during the administration of the given anesthetic compound to more accurately track the effects of the given anesthetic compound and the actual brain state of the patient.

Since 1846 and the first public uses of ether as a means to control pain during surgical procedures, anesthesia, analgesics, and other administered compounds to control pain have been a mainstay of medicine. However, while the use of the anesthetic and the number of compounds with anesthetic properties in clinical use have grown astronomically since the initial uses of ether, the scientific understanding of the operation of the body when under anesthesia is still developing. For example, a complete understanding of the effects of anesthesia on patients and operation of the patient's brain over the continuum of "levels" of anesthesia is still lacking. As such, anesthesiologists are trained to recognize the effects of anesthesia and extrapolate an estimate of the "level" of anesthetic influence on a given patient based on the identified effects of the administered anesthesia.

Unfortunately, there are a great number of variables that can influence the effects, effectiveness, and, associated therewith, the "level" of anesthetic influence on a given patient. Obvious variables include physical attributes of the patient, such as age, state of general health, height, or weight, but also less obvious variables that are extrapolated, for example, based on prior experiences of the patient when under anesthesia. When these variables are compounded with the variables of a given anesthesiologists' practices and the variables presented by a particular anesthetic compound or, more so, combination of anesthetic compounds, the proper and effective administration of anesthesia to a given patient can appear to be an art and a science.

Therefore, it would be desirable to have a system and method for reducing the unpredictability of administering anesthetic compounds to patients. More particularly, it would be desirable to have systems and methods that aid an anesthesiologists or other clinician in recognizing, reducing, and/or controlling the number of variable presented to the clinician when administering anesthetic compounds to patients.

SUMMARY OF THE INVENTION

The present invention overcomes the aforementioned drawbacks by providing a system and method for determining the state of a patient's brain under anesthesia using readily-available monitoring information, such as from a patient's electroencephalography (EEG). The present invention recognizes that anesthetic compounds induce different signatures in physiological characteristics of the patient under anesthesia and aids interpretation of such information. Using the physiological characteristics and signatures associated with the selected anesthetic compound, the present invention aids the correlation of the physiological characteristics and signatures to a state of the patient's brain.

In accordance with one aspect of the present invention, a system for monitoring a patient experiencing an administration of at least one drug having anesthetic properties is disclosed. The system includes a plurality of sensors configured to acquire physiological data from the patient and at least one processor. The processor is configured to assemble the physiological data into sets of time-series data associated with an origin location of the patient, transform each set of time-series data into a spectrum information, and determine coherence information with respect to the associated origin locations associated with the time-series of data. The processor is further configured to identify signatures within at least one of the spectrum information and the coherence information indicative of at least one of a current state and a predicted future state of the patient and generate a report using the signatures including information regarding at least one of the current state and the predicted future state of the patient induced by the drug.

In accordance with another aspect of the present invention, a system for monitoring a patient experiencing an administration of at least one drug having anesthetic properties is disclosed. The system includes a plurality of sensors configured to acquire physiological data from the patient, a user interface configured to receive an indication of at least one of a characteristic of the patient and the at least one drug having anesthetic properties, and at least one processor. The processor is configured to identify signature profiles indicative of at least one of a current state and a predicted future state of the patient based on the indication and assemble the physiological data into sets of time-series data. The processor is further configured to analyze the sets of time-series data using the identified signature profiles and generate a report including information regarding at least one of the current state and the predicted future state of the patient induced by the drug.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 9A, 9B, 9C, 9D, 9E and 9F show a collection of EEG waveforms and spectrograms illustrating key markers within the data and reflected in each data format.

DETAILED DESCRIPTION OF THE PREFERRED EMBODIMENT

The present invention recognizes that anesthetic compounds induce different signatures in physiological characteristics of the patient under anesthesia and aids interpretation of physiological characteristics and signatures therein based on a selected anesthesia compound. Using the physiological characteristics and signatures associated with the selected anesthesia compound, the present invention aids the correlation of the physiological characteristics and signatures to a state of the patient's brain.

Figure 1:
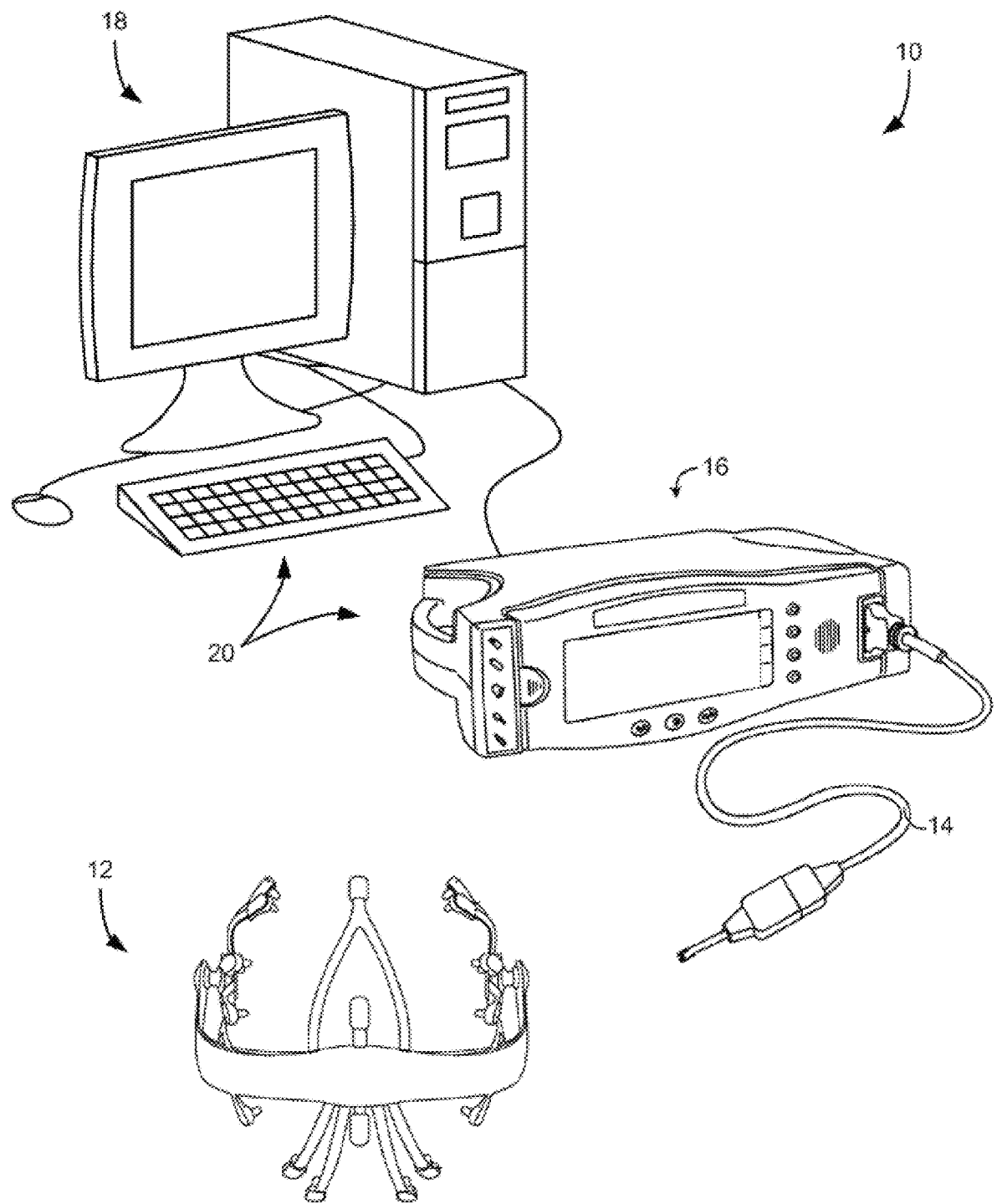
FIG. 1 is a schematic illustration of a system for determining the state of a patient's brain under anesthesia in accordance with the present invention.

For example, turning to FIG. 1, a system 10 configured for use in accordance with the present invention includes a patient monitoring device 12, such as a physiological monitoring device, illustrated in FIG. 1 as an electroencephalography (EEG) electrode array. However, it is contemplated that the patient monitoring device may also include mechanisms for monitoring galvanic skin response (GSR), for example, to measure arousal to external stimuli. One specific realization of this design utilizes a frontal Laplacian EEG electrode layout with additional electrodes to measure GSR. Another realization of this design incorporates a frontal array of electrodes that could be combined in post-processing to obtain any combination of electrodes found to optimally detect the EEG signatures described earlier, also with separate GSR electrodes. Another realization of this design utilizes a high-density layout sampling the entire scalp surface using between 64 to 256 sensors for the purpose of source localization, also with separate GSR electrodes.

The patient monitoring device 12 is connected via a cable 14 to communicate with a monitoring system 16. Also, cable 14 and similar connections can be replaced by wireless connections between components. As illustrated, the monitoring system 16 may be further connected to a dedicated analysis system 18. Also, the monitoring system 16 and analysis system 18 may be integrated.

For example, as noted above, it is contemplated that the patient monitoring device 12 may be an EEG electrode array, for example, a 64-lead EEG electrode array. However, as will be apparent below, greater spatial accuracy can be achieved by increasing the number of electrodes from 64 to 128, 256, or even higher. Similarly, the present invention can be implemented with substantially less electrodes. In any case, the monitoring system 16 may be configured to receive raw signals acquired by the EEG electrode array and assemble, and even display, the raw signals as EEG waveforms. Accordingly, the analysis system 18 may receive the EEG waveforms from the monitoring system 16 and, as will be described, analyze the EEG waveforms and signatures therein based on a selected anesthesia compound, determine a state of the patient based on the analyzed EEG waveforms and signatures, and generate a report, for example, as a printed report or, preferably, a real-time display of signature information and determined state. However, it is also contemplated that the functions of monitoring system 16 and analysis system 18 may be combined into a common system.

Figure 2:
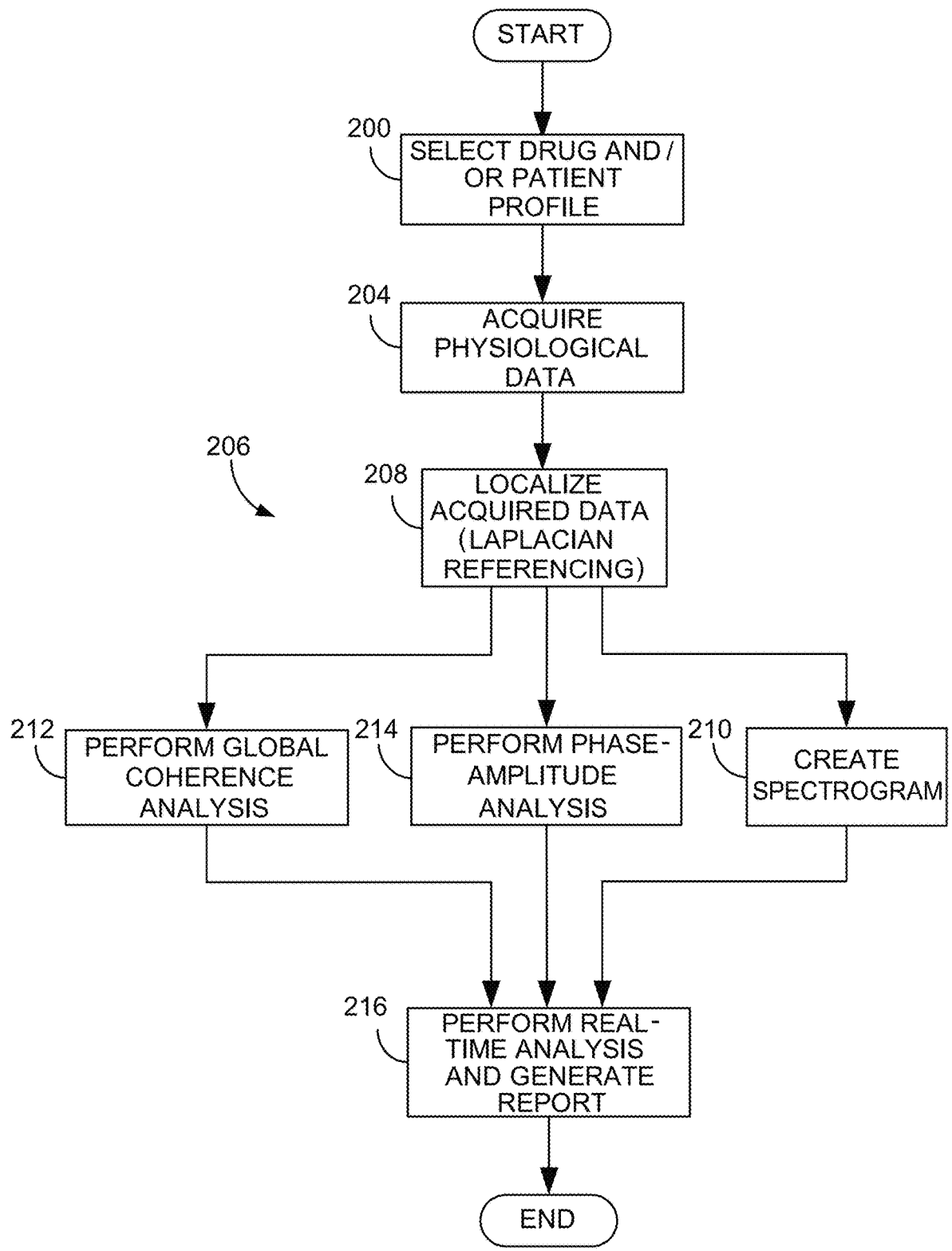
FIG. 2 is a flow chart setting forth the steps of a method for determining the state of a patient's brain under anesthesia in accordance with the present invention

Referring to FIG. 2, a method for analysis and reporting in accordance with the present invention begins at process block 200 with the selection of a desired drug, such as anesthesia compound or compounds, and/or a particular patient profile, such as a patient's age height, weight, gender, or the like. Such selection may be communicated through a user interface 20 of FIG. 1. Furthermore, drug administration information, such as timing, dose, rate, and the like, in conjunction with the above-described EEG data may be acquired and used to estimate and predict future patient states in accordance with the present invention. As will be described, the present invention recognizes that the physiological responses to anesthesia vary based on the specific compound or compounds administered, as well as the patient profile. For example, elderly patients have a tendency to show lower amplitude alpha power under anesthesia, with some showing no visible alpha power in the unconscious state. The present invention accounts for this variation between an elderly patient and a younger patient. Furthermore, the present invention recognizes that analyzing physiological data for signatures particular to a specific anesthetic compound or compounds administered and/or the profile of the patient substantially increases the ability to identify particular indicators of the patient's brain being in a particular state and the accuracy of state indicators and predictions based on those indicators.

Figure 15:
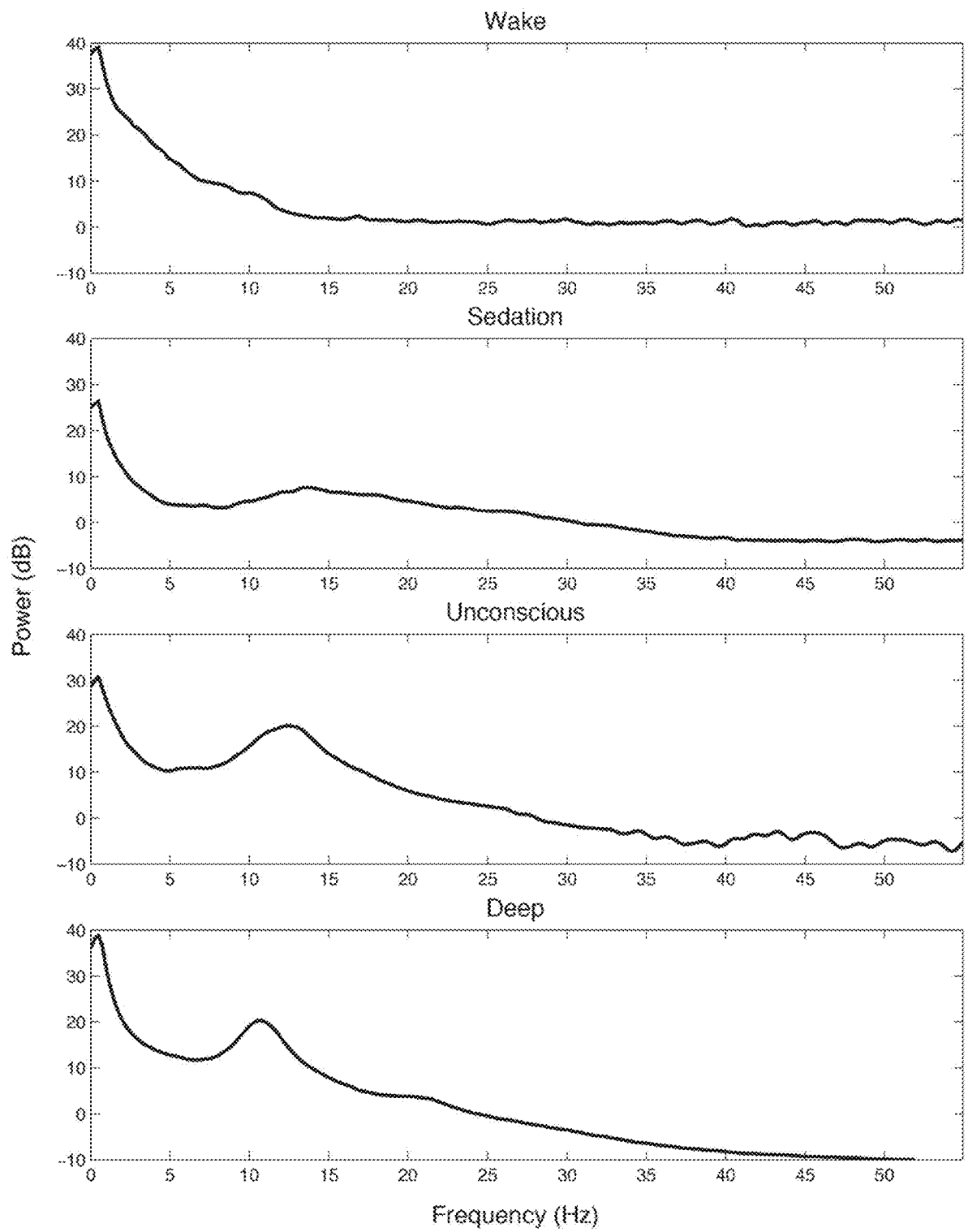

For example, the following drugs are examples of drugs or anesthetic compounds that may be used with the present invention: Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifenanil, Fentanyl, Sufentanil, Alfentanil, and the like. However, the present invention recognizes that each of these drugs, induces very different characteristics or signatures, for example, within EEG data or waveforms. For example, FIG. 15 provides EEG data for one prominent drug, propofol, and associated states.

Figure 3A:
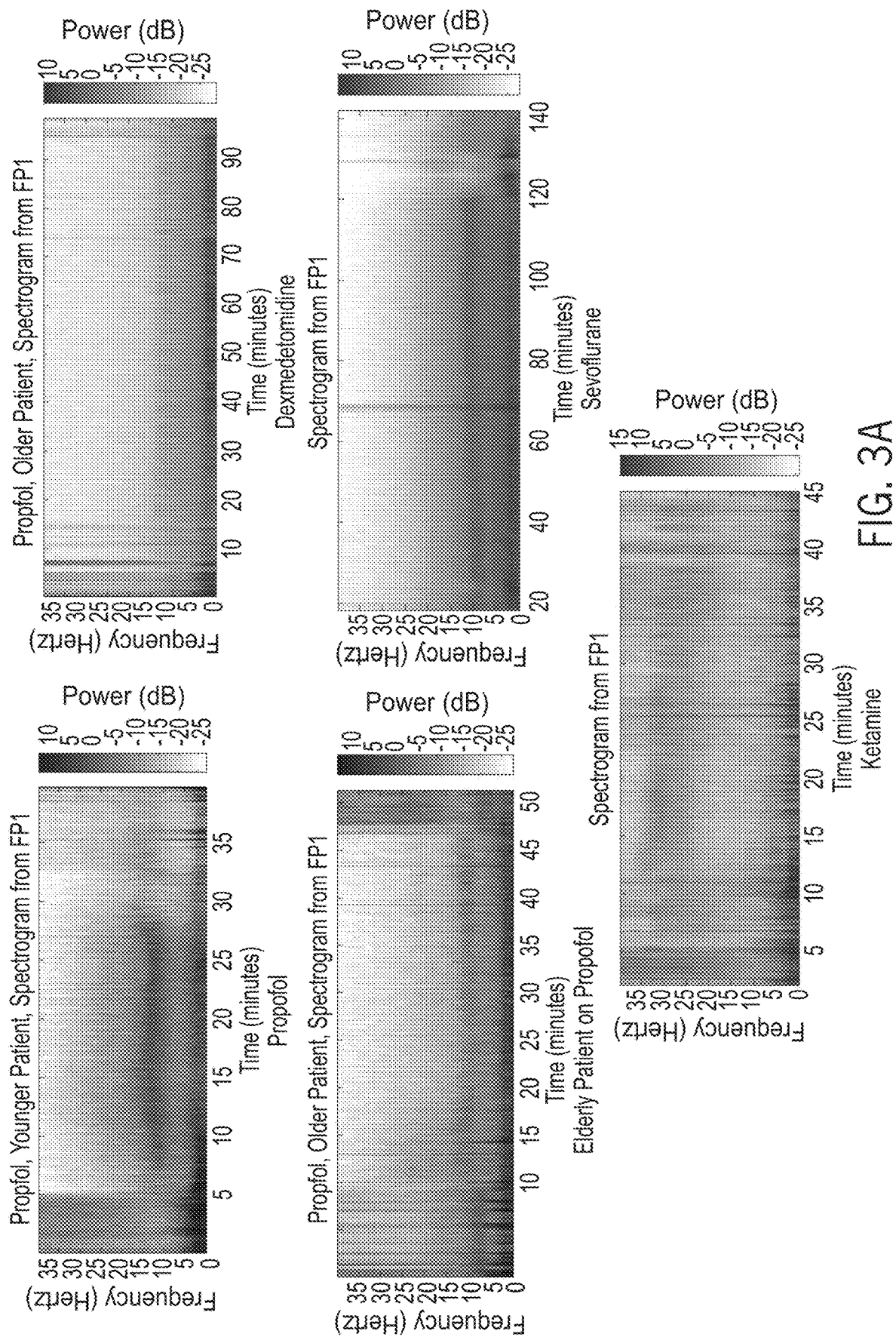
FIG. 3A is a series of spectrograms acquired under different drug or patient characteristics.
Figure 3B:
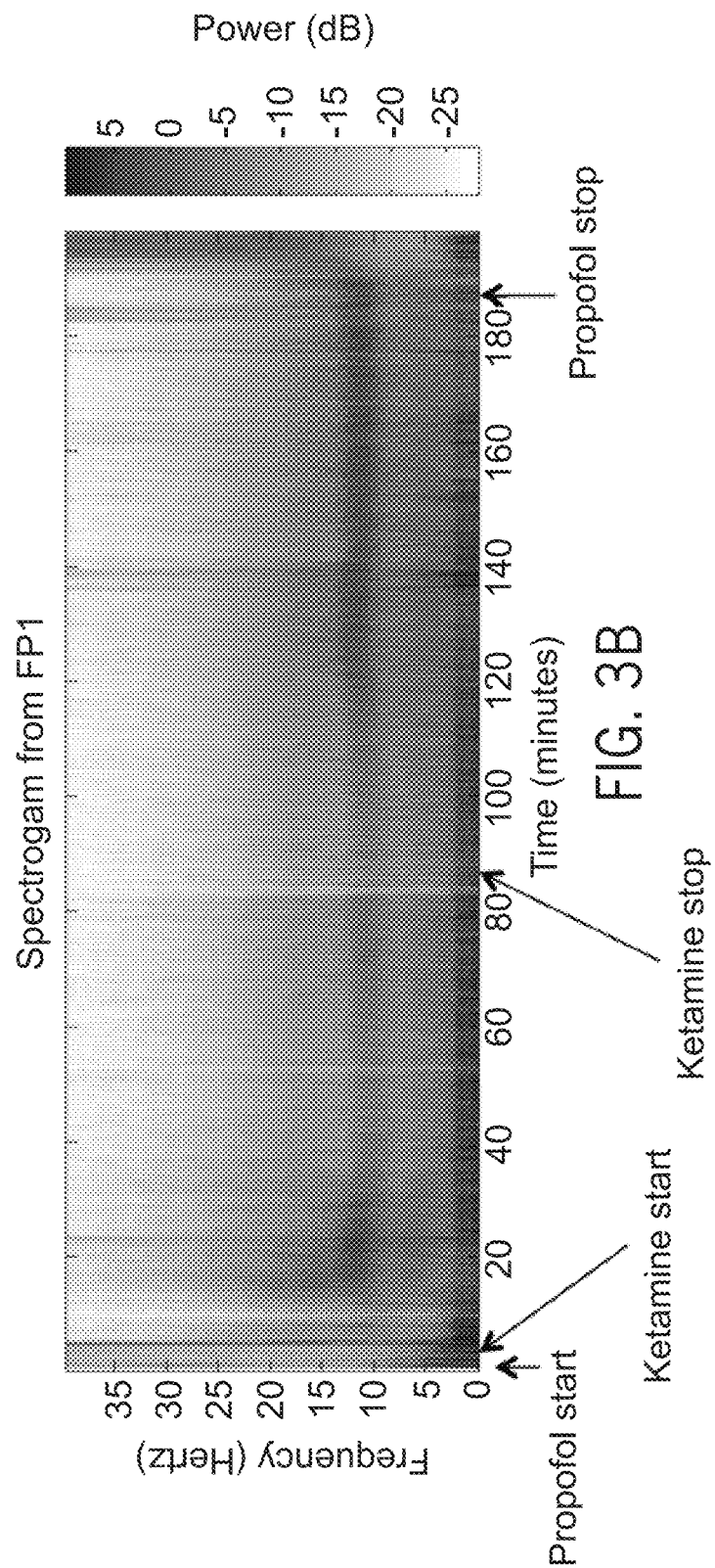
FIGS. 3B, 3C and 3D show a spectrogram and associated EEG waveforms showing the overlapping influence of different drugs administered to a patient.
Figure 3C:
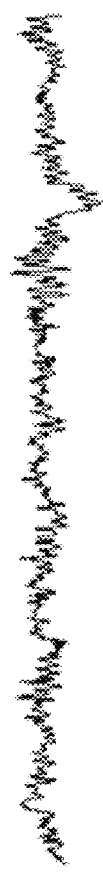
Figure 3D:

More particularly, referring to FIG. 3A, a plurality of spectrograms corresponding, as labeled, to patients having been administered Propofol, Dexmedetomidine, Sevoflurane, and Ketamine are illustrated. In addition, FIG. 3A shows a spectrogram of an elderly patient. When placed in proximity to one another, it is clear that the spectrograms vary substantially, so as to be visually distinct, based on the administered drug and/or patient profile. This is particularly true, for example, when multiple drugs are combined, such as illustrated in FIGS. 3B-3D. As will be explained, the present invention recognizes the substantial variation in physiological data acquired from a patient and the signatures contained therein. Based on a selected drug or drugs and/or the patient profile and, by taking this recognition into account, the present invention provides systems and methods for tracking brain states during the administration of anesthesia that is greatly improved over traditional systems. A summary of exemplary "spectral templates" for each of a plurality of exemplary drugs is provided in the "examples" section. These "spectral templates" can be used to automatically identify a current or project a future state of the patient.

Figure 4A:
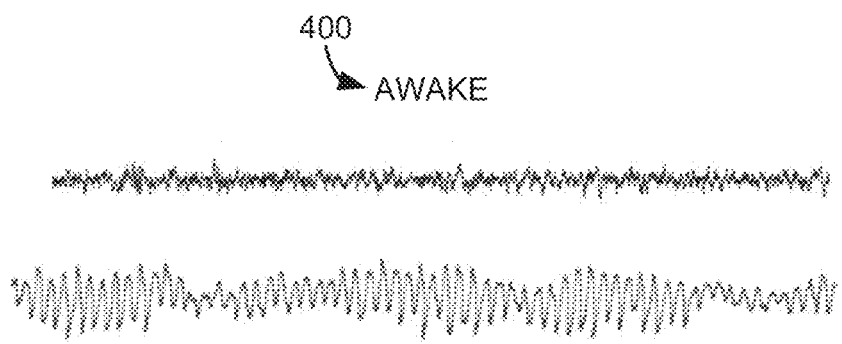
FIGS. 4A, 4B and 4C show a series of EEG waveforms collected to illustrate variations therein that can be observed as corresponding with respective patient states.
Figure 4B:
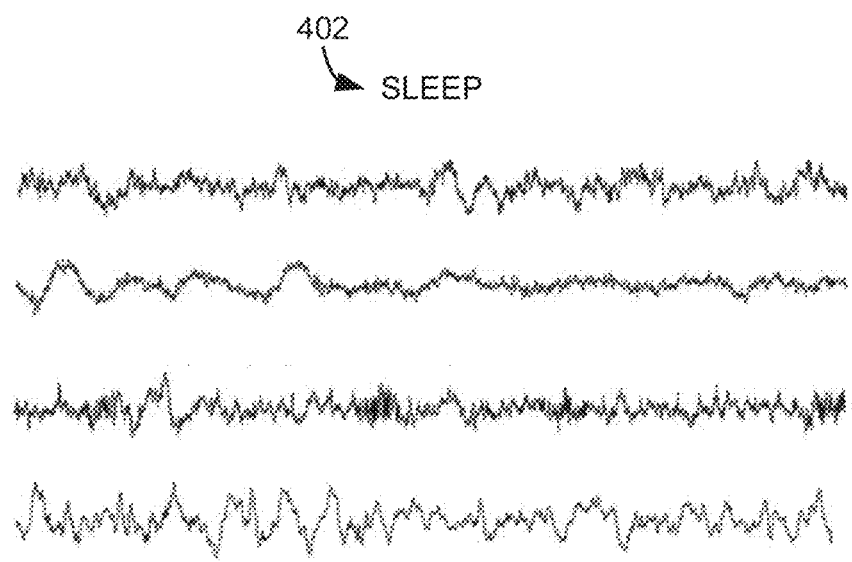
Figure 4C:
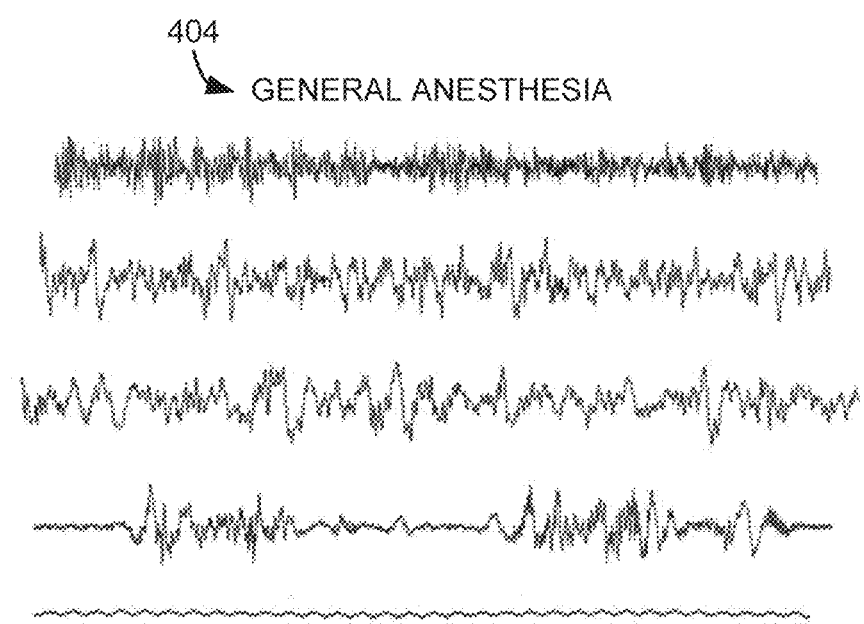

With the proper drug or drugs and/or patient profile selected, acquisition of physiological data begins at process block 204, for example, using a system such as described with respect to FIG. 1, where the acquired data is EEG data. Referring to FIGS. 4A-4C, a series of EEG waveforms in the time domain are illustrated. As is clear in a side-by-side comparison such as illustrated in FIGS. 4A-4C, these EEG waveforms vary appreciably. For example, general categories of "awake" 400 (FIG. 4A), "asleep" 402 (FIG. 4B), and under "general anesthesia" 404 (FIG. 4C) can be readily created. In the side-by-side comparison with the associated category titles 400, 402, 404 indicating the state of the patient when the EEG waveform was collected, one can see that there are general, distinguishing characteristics of the EEG waveforms within each category 400, 402, 404. However, when the EEG waveforms are not categorized or assembled with comparative EEG waveforms that provide a context for evaluating a given EEG waveform, distinguishing between or abstractly categorizing the EEG waveforms is very difficult. Thus, as will be described, the present invention provides systems and methods for analyzing acquired physiological information from a patient, analyzing the information and the key indicators included therein, and extrapolating information regarding a current and/or predicted future state of the patient.

Figure 5A:
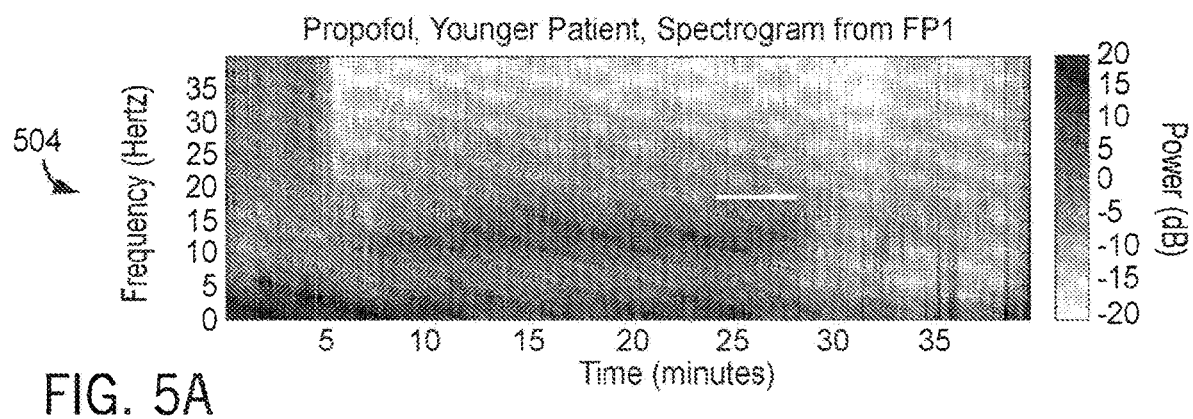
FIGS. 5A, 5B, 5C and 5D show a collection of data readouts including EEG waveforms, a frequency analysis, and a spectrogram illustrating key markers within the data and reflected in each data readout.
Figure 5B:
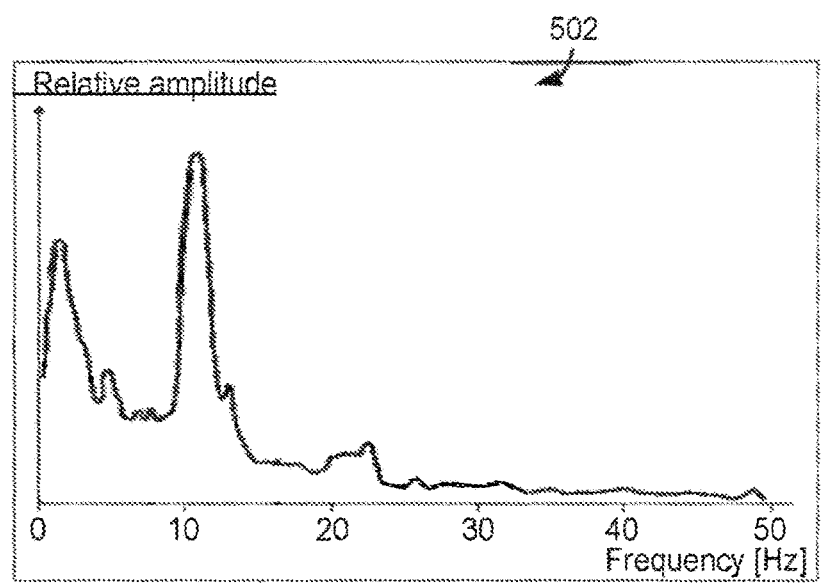
Figure 5C:
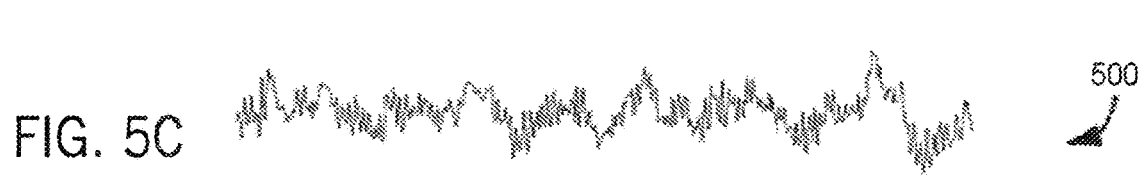
Figure 5D:

To do so, rather than evaluate physiological data in the abstract, at process block 206, the physiological data is processed. Processing can be done in the electrode or sensor space or extrapolated to the locations in the brain. As will be described, the present invention enables the tracking of the spatiotemporal dynamics of the brain by combining spectrogram and global coherence analyses. As will be apparent, reference to "spectrogram" in may refer to a visual representation of frequency domain information, such as represented in, for example, FIG. 3A. However, a "spectrogram" within the context of the present invention need not be visually represented or displayed. Rather, within the context, for example, of processing and report generation, the spectrogram may be an intermediate processing step from which reports or visual representations are ultimately created. For example, referring to FIGS. 5A-5D, EEG waveforms in the time domain 500 (FIGS. 5C-5D) have a spectrum 502 (FIG. 5B) and can be translated into a spectrogram 504 (FIG. 5A). However, rather than simply analyzing the spectrum information of the spectrogram 504 or a given spectrum 502 in the abstract, Laplacian referencing can be performed at process block 208 to estimate radial current densities perpendicular to the scalp at each electrode site of, for example, the monitoring device 12 of FIG. 1. Accordingly, though "spectrogram" processing is performed, a visual representation of the spectrogram need not be displayed.

Surface Laplacian calculations can be determined by taking a difference between voltages recorded at an electrode site and an average of the voltage recorded at the electrode sites in a local neighborhood. Denoting the voltage recorded at the $i^{th}$ electrode relative to a reference electrode located close to the top of the head as $V_i(t)$, the surface Laplacian of $V_i(t)$ can be estimated as:

$$J_i(t) \equiv V_i(t) - \frac{1}{M}\sum_{m=1}^{M} V_i^m(t), \qquad \text{Eqn. 1}$$

where $V_i^m(t)$ denotes the voltage recording at the $m^{th}$ closest electrode to electrode i. Thus, the EEG recorded at a particular location was locally referenced to an average of the EEG recorded at the neighbors. The choice of M depended on the nearest electrodes to $i^{th}$ electrode and on their locations' symmetry with respect to $i^{th}$ electrode. For the electrode on the top of the head, which had six symmetrically distributed nearest electrodes, M=6. For the remaining electrodes it is possible to find four or five neighbors that are arranged in an approximately symmetric configuration. In this case, M can be chosen to be equal to 4 or 5, respectively. For the electrodes at the edge, for which such a symmetric configuration cannot be approximated, surface Laplacian can be uncalculated and radial current density estimates not made. Accordingly, more accurate estimates of radial current density can be computed by increasing the number of electrodes and by accounting for the curvature of the head in the neighborhood of each electrode site.

Figure 6:
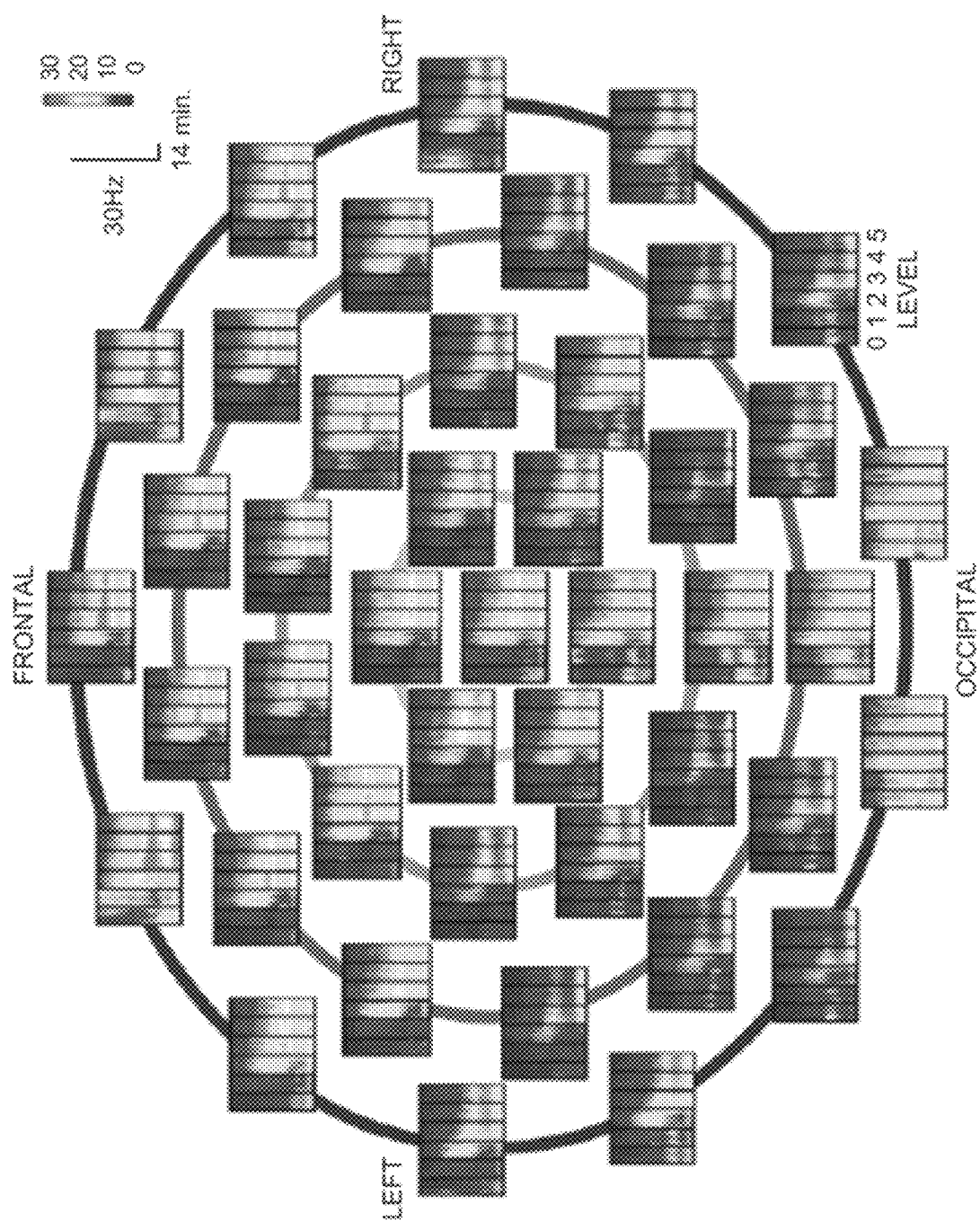
FIG. 6 is a collection of spectrograms of the radial current density estimated at each of a plurality of electrode sites.
Figure 7A:
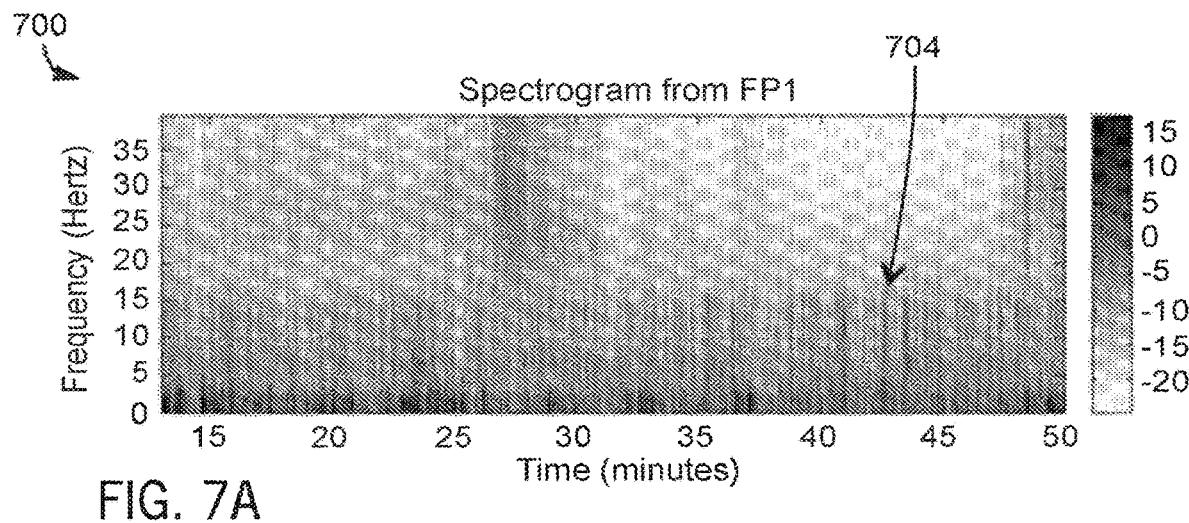
FIGS. 7A, 7B, 7C and 7D show a collection of EEG waveforms and spectrograms illustrating key markers within the data and reflected in each data format.
Figure 7B:
Figure 7C:
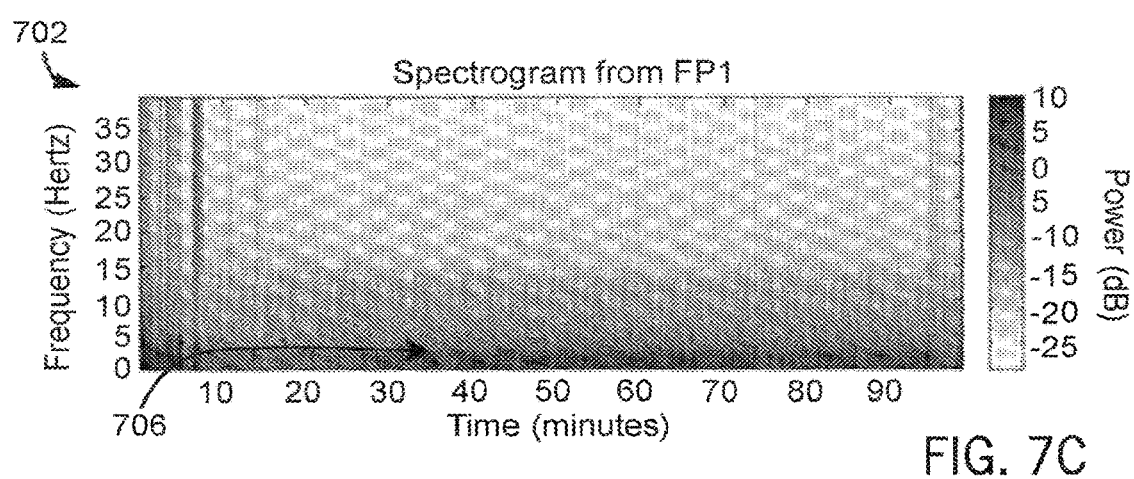
Figure 7D:
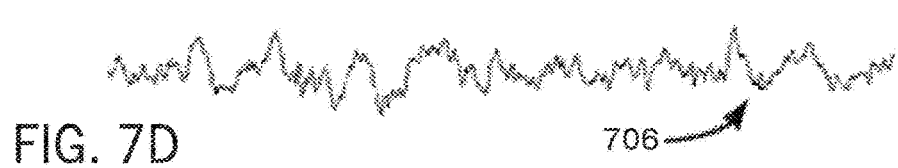

From these current density estimates, at process block 210, spectrograms at each electrode site are computed. Referring to FIG. 6, spectrograms of the radial current density estimated at each of a plurality of electrode sites are illustrated. As explained above, the spectrograms reflect, as illustrated in FIGS. 7A-7D, key signatures commonly identified or tracked in the time domain EEG waveforms. Specifically, two time domain EEG waveforms and associated spectrograms are illustrated, one set 700 corresponding to light Dexmedetomine sedation (FIGS. 7A-7B) and one set 702 corresponding to deep Dexmedetomine sedation (FIGS. 7C-7D). In the set 700 corresponding to light Dexmedetomine sedation, spindles 704 are visible and in the set 702 corresponding to deep Dexmedetomine sedation, strong slow wave oscillations 706 are visible.

It is noted that the local referencing is preferable so that distinct temporal patterns in the spectrogram at different electrode sites can be identified. This is in contrast to an average or single electrode referencing scheme, which would lead to an erroneous conclusion that approximately the same temporal pattern was present in the spectrogram at each electrode site.

The spectrum of the surface Laplacian at the location of the $i^{th}$ electrode site is estimated by averaging over K non-overlapping segments:

$$S_i^X(f) = \frac{1}{K}\sum_{k=1}^{K} X_i^k(f) X_j^k(f)^*; \qquad \text{Eqn. 2}$$

where $$X_i^k(f) \equiv Z_j^k(f) - \frac{1}{K}\sum_{k=1}^{K} Z_i^k(f)$$

is the mean corrected Fourier transform of the current density estimate at electrode site i of segment k at frequency f, and $X_i^k(f)^*$ is the complex conjugate.

To characterize the coordinated activity in the time-series of acquired data, an eigenvalue decomposition can be computed of a cross-spectral matrix at each spectral frequency as a function of time. Specifically, at process block 212, spectral and eigenvalue-based global coherence analyses can be used to track the spatiatemporal dynamics of the brain's anesthetic state. Generally, for the example of propofol, the global coherence analysis detects strong coordinated a activity in the occipital sites when the patient is awake that shifts to the frontal sites when the patient becomes unconscious.

In particular, method-of-moments estimates of the $i^{th}$ element of the cross-spectral matrix at a frequency f can be computed as:

$$C_{ij}^X(f) = \frac{1}{K}\sum_{k=1}^{K} X_i^k(f)X_j^k(f)^*;$$ Eqn. 3 where $X_i^k(f)$ and $X_j^k(f)$ are the tapered Fourier transforms of the current density estimates from electrode sites i and j, respectively, at frequency f. For N locations, $C^X(f)$ is an N×N matrix of cross-spectra.

An orthogonal basis can be obtained by performing a Karhunen-Loeve transform at each frequency, f:

$$Y^*(f) = U(f)^H X^*(f)$$ Eqn. 4 where $U(f)^H$ is the adjoint of the matrix U(f) (that is, the complex conjugate transpose of U(f), $U(f)^H = (U(f)^*)^T$) and a unitary matrix (that is, $U(f)U(f)^H = 1$). $U(f)^H$ is chosen so that under the Karhunen-Loeve transform the cross-spectral matrix in the new basis:

$$C_{ij}^Y(f) = \frac{1}{K}\sum_{k=1}^{K} Y_i^k(f)Y_j^k(f)^*;$$ Eqn. 5 is diagonal (that is, $C_{ij}^Y(f) = C_{ij}^Y(f)\delta_{ij}$. This implies that the diagonal elements of $C^Y(f) = S_i^Y(f)$, where $$S_i^Y(f) = \frac{1}{K}\sum_{k=1}^{K} Y_i(f)Y_i(f)^*$$

is the $i^{th}$ eigenvector, and the $i^{th}$ column of U(f) is the normalized eigenvector satisfying $\Sigma_{j=1}^N |U_{ji}(f)|^2 = 1$. Therefore, $|U_{ji}(f)|^2$ contains the contribution from the $i^{th}$ electrode to the $i^{th}$ eigenvector. The matrix whose $j^{th}$ and $i^{th}$ element is $|U_{ji}(f)|^2$ is termed the weighting matrix.

Sorting the eigenvalues, $S_1^Y(f) \geq S_2^Y(f) \geq \ldots \geq S_N^Y(f)$, the ratio of the largest eigenvalue to the sum of eigenvalues is:

$$C_{Global}(f) = \frac{S_1^Y(f)}{\sum_{i=1}^{N} S_i^Y(f)}.$$ Eqn. 6

This ratio is called the global coherence. When the leading eigenvalue is large compared with the remaining ones, $c_{Global}(f)$ is close to 1. In this case, examining the contributions of different sites to the corresponding eigenvector by using the elements of the weight matrix provides a summary of coordinated activity at this frequency. These elements are row weights. The row weights can be obtained by the absolute value square of the elements of the row of $U(f)^H$, which leads to the eigenvector with the highest eigenvalue.

Estimates of the cross-spectral matrix as described above can be sensitive to noise. To make cross-spectral estimation more robust, the median can be used in place of the mean in equation 5. The median is a robust estimator of centrality, and is much less sensitive to outliers than the mean.

Thus, process blocks 208-212 yield two pieces of valuable information, namely, the spectrogram and global coherence information, which show different spatiotemporal activity at different states of the patient receiving anesthesia. For example, for propofol, when patients are awake, the spectrograms will show strong occipital α activity. After loss of consciousness, the spectrograms will show a loss of α activity and an increase in δ activity in the occipital sites and strong α and δ activity in the frontal sites. Increased power in the α, β, and δ ranges in the frontal sites will occur after loss of consciousness, consistent with the well-known pattern of anteriorization. As patients lose responsiveness, the coordinated activity over the occipital sites in the a range diminish. When patients are unconscious, strong coordinated activity in the a range is observed broadly over the frontal electrode sites at which the spectrograms show the anteriorization pattern. Despite the overall high δ activity in the spectrograms, coordinated activity may only be observed in the α range. The relative power in the occipital α and δ ranges reliably track the patients' behavioral responses. For propofol, the occipital a power is greater than the δ power when the patient is awake, and the reverse is true when the patients are unconscious. The strong global coherence in the a range indicates highly coordinated activity in the frontal electrode sites. Thus, global coherence and weight matrices along with spectrograms provide a first level of data for determining a current state and predicting a future state of a patient's brain under anesthesia. Further details regarding initial testing and validation of such processes are provided in Cimenser A, Purdon P L, Pierce E T, Walsh J L, Salazar-Gomez A F, Harrell P G, Tavares-Stoeckel C, Habeeb K, Brown E N (2011) Tracking brain states under general anesthesia by using global coherence analysis. Proceedings of the National Academy of Sciences of the United States of America 108:8832-8837.

At process block 214, phase-amplitude analysis is performed that considers the amplitude of a given signal with respect to the phase of other signals and vice versa. As explained above, spectral analysis of EEG recordings allows the present invention to track systematic changes in the power in specific frequency bands associated with administration of anesthesia, including changes in δ (1-4 Hz), θ (5-8 Hz), α (8-14 Hz), β (12-30 Hz), and γ (30-80 Hz). However, spectral analysis treats oscillations within each frequency band independently, ignoring correlations in either phase or amplitude between rhythms at different frequencies.

Power spectral measures are invariant with respect to changes in the complex phase of a signal's Fourier transform. It is thus natural to extend power spectral analysis by using measures that are sensitive to signal phase. Bispectral analysis can detect the presence of correlation in the phases of oscillation at different frequencies. Bispectrum-based statistics have been used in quantitative clinical depth-ofanesthesia monitors, in a manner that compares the bispectrum across broad low- and high-frequency ranges.

However, in accordance with the present invention, instead of a traditional "cross-frequency correlation", phase-amplitude analysis, is used. In phase-amplitude analysis, the amplitude or envelope of activity in one frequency band is consistently largest at a particular phase of a lower frequency rhythm. For example, given two non-overlapping frequency bands, then in phase-amplitude coupling, the amplitude of the activity in the higher frequency band is consistently highest at a particular phase of the lower frequency rhythm. In accordance with the present invention, an analysis can be performed to measure phase-amplitude coupling in a time-resolved fashion to identify at least two distinct modes of phase-amplitude coupling corresponding to shallow and deep planes of anesthesia, respectively.

Specifically, to characterize coupling between the phase of the slow oscillation (SO; 0.1-1 Hz) and the amplitude of $\alpha$ (8-14 Hz) oscillations, a time-varying phase-amplitude modulogram $M(t, \phi)$ can be created that describes the relative $\alpha$ (or other) amplitude at a particular phase at each SO cycle.

Given an EEG signal, $x(t)$, sampled at rate $F_S=250$ Hz, ultra-low-frequency drift is removed by subtracting a least-square errors spline fit to the signal with one knot for every 2 minutes (or other selected duration) of data. Next, a band-pass filter may be applied to extract the rhythmic component within each frequency band of interest, $x_b(t)$, $b \in \{\alpha, SO\}$. Symmetric finite impulse response filters designed using a least-squares approach (SO: passband 0.1-1 Hz, transition bands 0.085-0.1 and 1-1.15 Hz, ≥17 dB attenuation in stop bands, order 2207 at 250 Hz; $\alpha$: passband 8-13.9 Hz, transition bands 5.9-8 and 13.9-16 Hz, ≥60 dB attenuation in stop bands, order 513) can be employed. A discrete Hilbert transform can be used to compute the complex analytic signal, $z_b(t)$, satisfying $\text{Re}[z_b(t)]=X_b(t)$. The analytic signal provides the instantaneous $\alpha$ amplitude $A(t)=|z.(t)|$ and SO phase, $\cdot(t)=\arg[z_{SO}(t)]$.

The modulogram is computed by assigning each temporal sample to one of, for example, 18 equally spaced phase bins based on the instantaneous value of $\psi(t)$, then averaging the corresponding values of $A(t)$ within, for example, a 2-minute epoch:

$$M(t, \phi) = \frac{\int_{t-\frac{\delta t}{2}}^{t+\frac{\delta t}{2}} \int_{\phi-\frac{\delta t}{2}}^{\phi+\frac{\delta t}{2}} A(t')\delta(\psi(t') - \phi')d\phi'dt'}{2\pi \int_{t-\frac{\delta t}{2}}^{t+\frac{\delta t}{2}} A(t')dt'}; \qquad \text{Eqn. 7}$$

where $\delta(t)=120$ s and $\delta\phi=2\pi/18$. Note that $\int_{-\pi}^{\pi} M(t, \phi)d\phi=1$, so that $M(t, \phi)$ is a normalized density of a amplitude over all SO phases.

For example, FIGS. 8A-8D illustrate two distinct patterns of phase-amplitude modulation. Namely, a first phase-amplitude modulation is similar to slow wave sleep (peak-max—i.e., high-frequency activity is highest at the peak of the low-frequency oscillation, corresponding to a low-frequency phase of 0), and a second phase-amplitude modulation foreshadows the return of consciousness (trough-max -i.e., high-frequency activity is highest at the trough of the low-frequency oscillation, corresponding to a low-frequency phase of $+/-\pi$). Slow oscillation phase modulates alpha/beta (8-14 Hz) amplitude, in relation to probability of response, can be studied and is reflected in FIG. 8A.

Figure 8A:
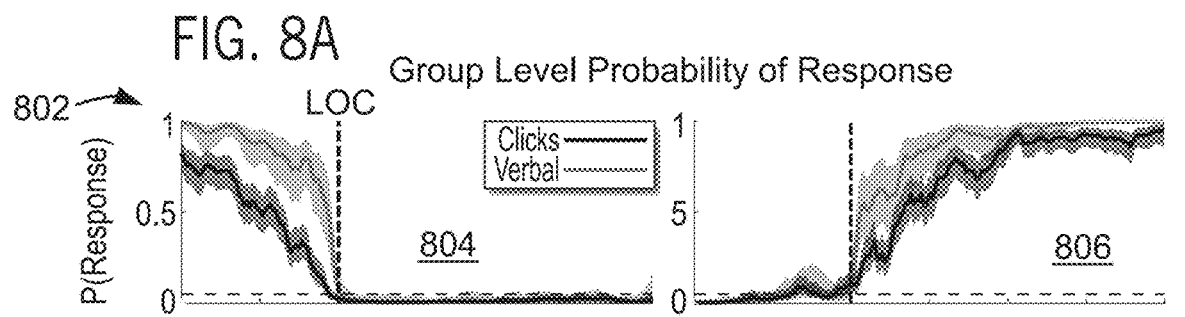
FIGS. 8A, 8B, 8C and 8D show a set of graphs, phase-amplitude histograms, and EEG waveforms illustrating phase-amplitude analysis as a mechanism for determining and predicting future patient states.
Figure 8B:
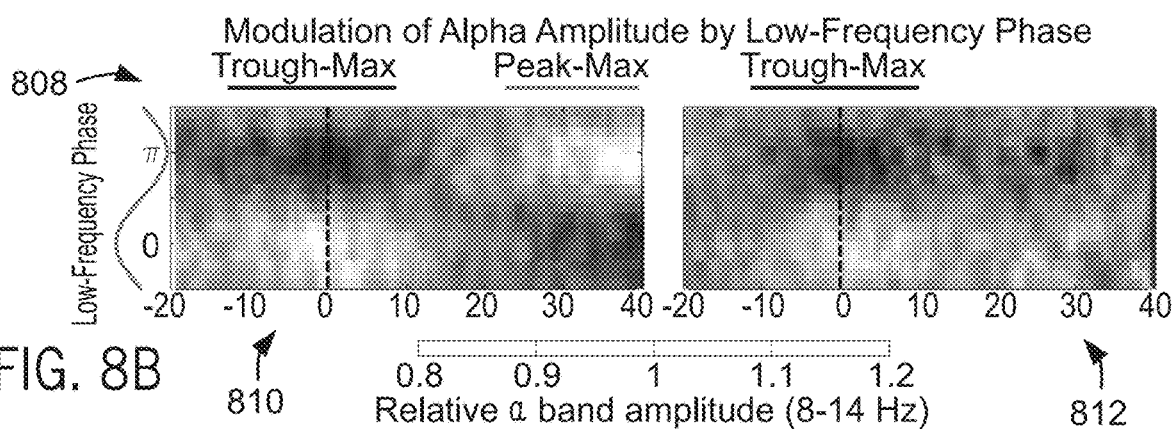
Figure 8C:
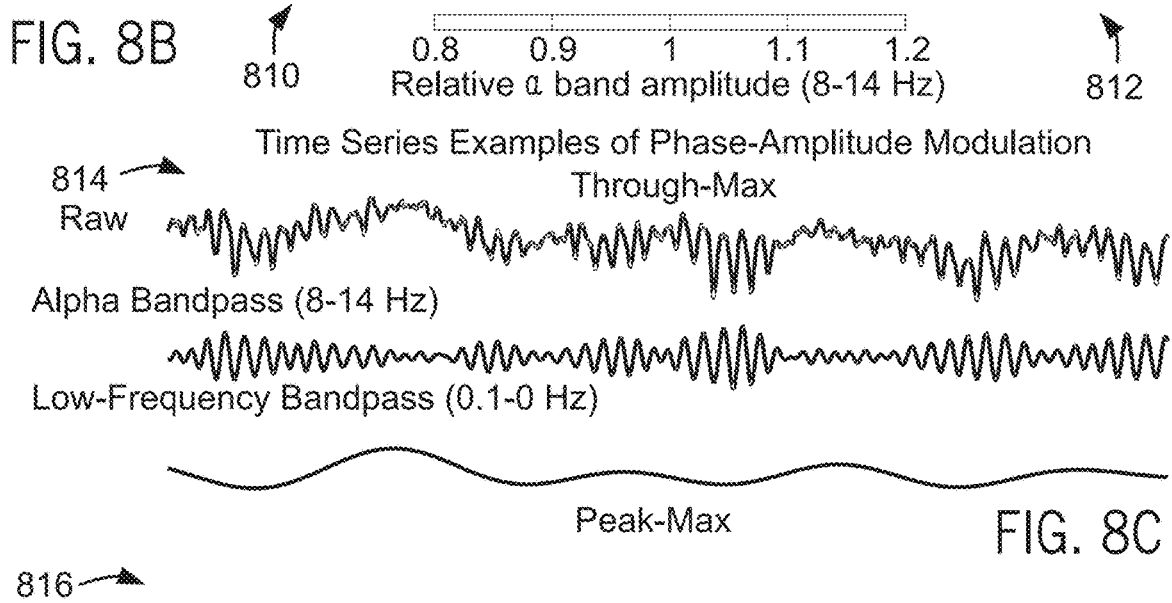
Figure 8D:
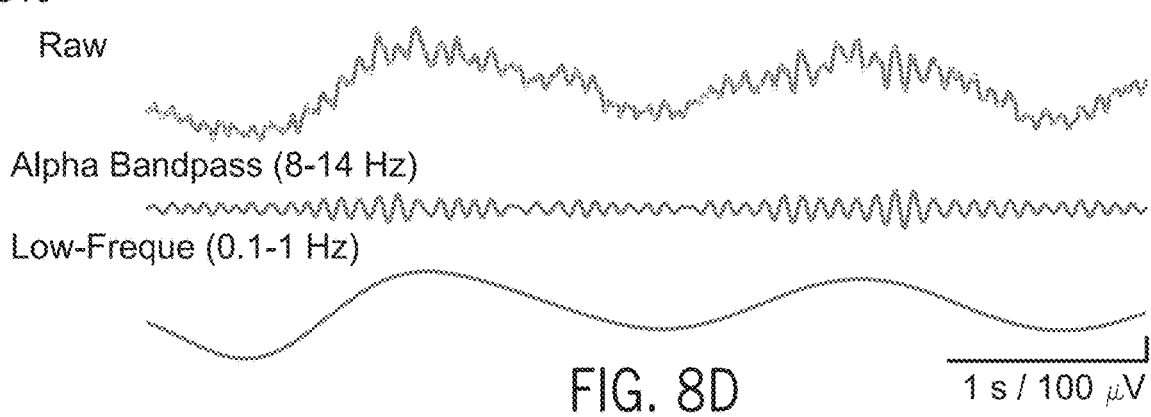

Specifically, group behavioral curves 802 show the probability of response to click and verbal stimuli during induction in the first graph 804 and emergence in the second graph 806. As illustrated in FIG. 8B, a set of phase-amplitude histograms 808 shows the relationship between the slow oscillation phase (y-axis, shown with reference sinusoid) and mean-normalized alpha/beta amplitude as a function of time (x-axis) relative to LOC 810 and ROC 812. A trough-max phase-amplitude relationship can be observed at the LOC/ROC transition points, where the amplitude of alpha is maximal at the slow oscillation troughs. A peak-max phase-amplitude relationship can be observed during the unconscious state, where the amplitude of alpha is maximal at slow oscillation peaks. These modulation patterns can be observed in the raw EEG traces 814 and 816 of FIGS. 8C and 8D, which show the trough-max and the peak-max, respectively. The trough-max pattern re-appears during emergence prior to ROC, illustrating that it can be used to predict when patients are able to regain consciousness during anesthesia.

For example, because the transition to the trough-max pattern occurs reliably before return of consciousness, the trough-max relationship to predict when patients are likely to recover consciousness while emerging from anesthesia. In cases where trough-max modulation is absent, due to pathology that impairs alpha waves, or drug choice (e.g., sevoflurane), or where electrode placement makes detection of trough-max modulation difficult, the absence or loss of peak-max modulation could also be used to predict recovery of consciousness during emergence. More particularly, during emergence from propofol anesthesia, the peak-max modulation relationship between the phase of the slow oscillation and higher frequencies changes to the trough-max modulation relationship, and does so prior to the return of consciousness, with little change to the underlying power spectrum. The trough-max modulation has a frontal distribution, whereas the peak-max modulation is distributed approximately uniformly across the scalp.

Thus, such phase-amplitude information can provide a reliable indicator of a current or probable future patients state. For example, since the peak-max modulation pattern represents a state of unconsciousness that is more profound than that observed during trough-max modulation, but less profound than burst-suppression, the peak-max modulation pattern could be used as a target for maintenance of a surgical level of anesthesia. Because the trough-max modulation represents a state of unconsciousness that is less profound than the peak-max modulation, one where patients can respond to external stimuli, the trough-max modulation pattern could be used as a target for maintenance of sedation. Furthermore, as described above, elderly patients often exhibit diminished alpha waves or a lack of alpha waves. Hence, in elderly patients who show diminished alpha waves, or who lack alpha waves, monitoring can also be performed by calculating slow oscillation phase-amplitude modulation across a broad-band frequency range including theta, alpha, beta, and gamma bands.

To quantify the strength of modulation, a modulation index, $M(t)$ can be defined, as the Kullback-Leibler divergence, in bits, between $M(t, \phi)$ and a uniform phase distribution over the interval $(-\pi, \pi)$:

$$MI(t) = \int_{-\pi}^{\pi} \frac{M(t, \phi)}{2\pi} \log_2 M(t, \phi) d\phi. \qquad \text{Eqn. 8}$$

It is noted that the power spectrum and phase-amplitude coupling may be complementary sources of information about brain dynamics. Thus, a combination of both measures may reveal greater structure than either analysis alone.

For example, the EEG power spectrum during gradual administration of anesthesia shows a broad-band peak that begins in gamma frequencies, and decreases in frequency and bandwidth into the low-beta and alpha bands with increasing doses of anesthesia resulting in loss of consciousness. The gamma and beta range effects are associated with a reduced probability of response to external stimuli. Power within this traveling peak is strongest in frontal EEG channels. This reverses after recovery of consciousness. The traveling peak frequency can be quantified, for example, as the median between 2 and 40 Hz, and calculate the bandwidth using the interquartile range between the same limits.

It is further noted that the above-described phase-amplitude modulation effect and systems and methods for monitoring thereof is best observed using a local average of several electrodes, such as the surface Laplacian. Otherwise, phase-amplitude modulation effect can be poorly resolved or not observable.

In accordance with one configuration of the present invention, a beamforming procedure may be used to improve estimation of phase-amplitude modulation, Let $x(t):=[x_1(t), x_2(t), \ldots, x_N(t)]^T$ denote the EEG time-series corresponding to N EEG channels for time $0 \le t \le T$. Let $\alpha(t):=[\alpha_1(t), \alpha_2(t), \ldots, \alpha_N(t)]^T$ and $s(t):=[s_1(t), s_2(t), \ldots, s_N(t)]^T$ denote the alpha rhythm and slow oscillation time-series which are obtained by band-pass filtering $x(t)$ in the frequency bands of 8-14 Hz and 0.1-1 Hz, respectively. Let $\alpha^H(t):=\alpha(t)+i\mathcal{H}(\alpha(t))$ and $s^H(t):=s(t)+i\mathcal{H}(s(t))$, where $\mathcal{H}(\cdot)$ is the discrete-time Hilbert transform. The amplitude of the alpha rhythm is modulated by the phase of the slow oscillation during anesthesia, based on an analysis of single-channel Laplacian-derived EEG.

Assuming that the phase-amplitude modulation arises from a unified and possibly spatially localized mechanism in the brain, the problem reduces to reconstructing a single phase-amplitude modulation relationship based on the observation through the multi-channel array of EEG sensors.

A viable solution is given by beamforming. The idea of beamforming is to form a scalar signal based on the array observations in order to minimize an appropriate cost function representing the underlying system model. Let $w:=[w_1, w_2, \ldots, w_N]^T$ denote a weight vector (beamforming vector) and consider the corresponding projection of the alpha rhythm and slow oscillation time series given by $\alpha_W(t):=w^T\alpha^H(t)$, and $s_W(t):=w^Ts^H(t)$, respectively. The amplitude of $\alpha_W(t)$ and the phase (argument) of $s_W(t)$ are given by:

$$A_W(t):=\sqrt{(\Sigma_{k=1}^N w_k\alpha_k(t))^2+(\Sigma_{k=1}^N w_k\overline{\mathcal{H}_k(\alpha_k(t))})^2} \quad \text{Eqn. 9; and}$$

$$\theta_W(t):=\arg(\Sigma_{k=1}^N w_k s_k(t)+\Sigma_{k=1}^N w_k\overline{\mathcal{H}}(s_k(t))) \quad \text{Eqn. 10;}$$

respectively. Suppose that for a given value of the phase of $s_W(t)$, denoted by $\theta$, the amplitude of the alpha rhythm $A_W(t)$ has a distribution given by the density $p_W(A; \theta)$. Then, the phase-amplitude modulation relation is defined as:

$$A_W(\theta;t):=E_{p_W}\{A_W(t)|\theta\} \quad \text{Eqn. 11}$$

where the ensemble averaging $E_{pw}$ is with respect to the density $p_W(A; \theta)$. The function $A(\theta;t)$ is clearly periodic with the full period defined as $[-\pi, \pi]$. Assume that $A(\theta;t)$ is stationary during the observation period $[0, T]$ and hence drop the dependence on t. Assuming that the function $A_W(\theta)$ has sufficient smoothness properties, it can be represented in the Fourier basis as follows:

$$A_w(\theta)=\overline{\omega}+\Sigma_{k=1}^\infty a_k \sin(k\theta)+b_k \cos(k\theta) \quad \text{Eqn. 12;}$$

where $\mu$, $a_k$, and $b_k$ denote the expansion coefficients. A suitable model for estimating $A_W(\theta)$ is given by its truncated Fourier expansion to the first L terms, with $L \le 3$. This reduced-order model enforces a smooth phase-amplitude modulation relation, which is consistent with empirical observations. A suitable cost function for estimating $A_W(\theta)$ is given by the following quadratic form:

$$R(\mu\{a_k, b_k\}; w):=\int_{k=1}^L\{A_W(\theta)-\mu-\Sigma_{k=1}^L(a_k \sin(k\theta)+b_k \cos(k\theta))\}^2 p(\theta)d\theta \quad \text{Eqn. 13.}$$

Since the densities $p_W(A; \theta)$ are unknown, it is not possible to compute $A_W(\theta;t):=E_{p_w}\{A_w(t)|\theta\}$. Hence, an empirical quadratic cost function can be used for estimating $A_W(\theta)$ by substituting the ensemble averaging operator $E_{pw}$ by the corresponding temporal averaging as follows:

$$R(\mu\{a_k, b_k\};w):=\int_{-\pi}^\pi\{E_T\{A_w(t_w(\theta))\}-\mu-\Sigma_{k=1}^L(a_k \sin(k\theta)+b_k \cos(k\theta))\}^2 p(\theta)d\theta \quad \text{Eqn. 14;}$$

where $t_w(\theta)$ denotes the inverse function of $\theta_w(t)$, $p(\theta)$ is the prior distribution of the slow oscillation phase and $E_t$ denotes temporal averaging.

Note, replacing ensemble averaging by temporal averaging implicitly assumes the ergodicity of the underlying processes during the observation period $[0, T]$. Since the prior $p(\theta)$ is unknown, the cost function can be further approximated by substituting the ensemble averaging over $\theta$ by the corresponding temporal averaging as follows:

$$\hat{R}_T(\mu, \{a_k, b_k\}; w) := \frac{1}{T}\sum_{t=0}^T \left\{ A_W(t) - \mu - \sum_{k=1}^L (a_k\sin(k\theta_W) + b_k\cos(k\theta_W)) \right\}^2. \quad \text{Eqn. 15}$$

For a given beamformer w, it is possible to minimize the cost function over the parameters $\mu$, $a_k$, and $b_k$. Then, the best such beamformer can be chosen by minimizing the resulting cost function over w. This, in fact, corresponds to a cost minimization formulation for estimating the reduced-order phase-amplitude modulation relation that is most consistent with the data (in the sense of the above quadratic cost function). Assuming that the beamformer elements are bounded as $\underline{w} \le w_k \le \overline{w}$, for some constants $\underline{w}$ and $\overline{w}$, the overall optimization procedure can be expressed as:

$$\min_w \min_{\mu, a_k, b_k} \hat{R}_T(\mu, \{a_k, b_k\}; w) \; s.t. \underline{w} \le w_k \le \overline{w}, \; \forall k \quad \text{Eqn. 16.}$$

The inner minimization can be carried out by linear regression and the resulting solution can be expressed explicitly in terms of $A_w(t)$ and $\theta_w(t)$. The outer minimization can be performed using standard optimization routines. In particular, since the constraints on $w_k$ form a convex set, the interior point method for the outer minimization stage can be employed.

Under the above-described process and with respect to, for example, propofol, it can be shown that the phase-amplitude modulation of frontal EEG under anesthesia undergoes two different patterns of modulation, corresponding to depth of anesthesia. The first pattern, occurring before and after the loss of consciousness, consists of maximum alpha amplitude occurring at the trough (surface-negative) of the slow oscillation, which can be referred to as the "trough-max" pattern. At deeper levels of anesthesia, the relationship reverses and maximum alpha amplitude occurs at the peak (surfacepositive) of the slow oscillation, which can be referred to as the "peak-max" pattern. In order to compute the electrode weights that would show both modes of the phase-amplitude modulation most clearly, equal-length segments of data from both modes were chosen and used to compute the optimal weights for each mode. These trough-max and peak-max data for the two patients were used to perform the averaging described in equation 15. The data used in the optimization consisted of four-minute segments, chosen as periods during which the phase-amplitude modulation was relatively constant, based on phase-amplitude histograms computed using Laplacian-referenced data. Table I illustrates modulation depths for different methodologies.

|  | Patient 1 | | Patient 2 | |
| --- | --- | --- | --- | --- |
|  | Trough-Max | Peak-Max | Trough-Max | Peak-Max |
| Bipolar | 0.26 | 0.39 | 0.22 | 0.76 |
| Laplacian | 1.08 | 0.73 | 0.98 | 1.00 |
| Optimized | 1.23 | 0.91 | 1.33 | 1.67 |

The beamforming method produced the largest modulation depth, followed by the Laplacian method, with bipolar referencing showing the lowest modulation depth in both regimes. Thus, The beamforming method provides a means to obtain electrode weights that minimize the least-squares error in a parametric sinusoidal model of the phase-amplitude relationship. This optimal weighting of EEG electrodes allows for improved detection of phase-amplitude modulation across time and patients. This method could be useful in studies of phase-amplitude modulation in the EEG under anesthesia, as well as other conditions where this phenomenon might arise.

The above-described selection of an appropriate analysis context based on a selected drug or drugs (process block 200), the acquisition of data (process block 204), and the analysis of the acquired data (process blocks 206-214) set the stage for the new and substantially improved real-time analysis and reporting on the state of a patient's brain as an anesthetic or combination of anesthetics is being administered and the recovery from the administered anesthetic or combination of anesthetics occurs. That is, although, as explained above, particular indications or signatures related to the states of effectiveness of an administered anesthetic compound or anesthetic compounds can be determined from each of the above-described analyses (particularly, when adjusted for a particular selected drug or drugs), the present invention provides a mechanism for considering each of these separate pieces of data and more to accurately indicate and/or report on a state of the patient under anesthesia and/or the indicators or signatures that indicate the state of the patient under anesthesia.

Specifically, referring to process block 216, any and all of the above-described analysis and/or results can be reported and, in addition, can be coupled with a precise statistical characterizations of behavioral dynamics. That is, behavioral dynamics, such as the points of loss-of-consciousness and recovery-of-consciousness can be precisely, and statistically calculated and indicated in accordance with the present invention. To do so, the present invention may use dynamic Bayesian methods that allow accurate alignment of the spectral and global coherence analyses relative to behavioral markers.

To build the information needed to achieve this, a study was performed to correlate the behavior marks with EEG information. With respect to the points of loss of consciousness and recovery of consciousness and any other desired points, three possible behavioral outcomes may be defined: correct responses, incorrect responses, and no response. A state-space model with two state variables representing a probability of response and a conditional probability of correct response can be used to correlate outcomes with a predicted future state. Probability densities of model parameters and the response probability are computed within a Bayesian framework to provide precise statistical characterizations of behavioral dynamics.

For example, assume the experiment consists of K stimulus trials. On any trial these are three possible outcomes for the response to the verbal stimulus: the subject may respond correctly, respond incorrectly or not respond. Let $m_k=1$ if the subject responds on trial k and 0 otherwise. If there is a response on trial k, let $n_k=1$ if it is correct and 0 otherwise. Let $p_k$ denote the probability of a response on trial k, i.e. that $n_k=1$, and $q_k$ denote the probability of a response of a correct response, i.e. $m_k=1$. The observed data at trail k is the pair $(m_k, n_k)$ which can assume the values $\{(1,1), (1,0), (0,0)\}$. The observation model at trail k is therefore:

$$Pr(m_k,n_k|p_k,q_k)=[p_k(q_k)^{1-n_k}]^{m_k}(1-p_k)^{1-m_k} \quad \text{Eqn. 17;}$$

Where we define $p_k$ and $q_k$ in terms of the cognitive state variables by the logistic relations:

$$p_k=[1+\exp(-x_k)]^{-1} \quad \text{Eqn. 18;}$$

$$q_k=[1+\exp(-z_k)]^{-1} \quad \text{Eqn. 19.}$$

We define state model for the unobservable cognitive state variables as the random walk equations:

$$x_k=x_{k-1}+\varepsilon_k \quad \text{Eqn. 20;}$$

$$z_k=z_{k-1}+\eta_k \quad \text{Eqn. 21;}$$

Where $\varepsilon_k$ and $\eta_k$ are zero-mean Gaussian random variables with variances $\sigma_\varepsilon^2 \Delta_k$ and $\sigma_n^2 \Delta_k$ where $\Delta_k$ is the time elapsed between verbal stimulus trials k−1 and k.

Formulating the probability of response and the conditional probability of a correct response on each trial as a logistic function of the cognitive state variable ensures that these probabilities are properly defined between 0 and 1. The state model provides a continuity constraint so that the current cognitive state and hence, the probability of a response and the conditional probability of a correct response depend on the previous cognitive state and experience. We let $\theta=\{\sigma_\varepsilon^2, \sigma_n^2, x_0, z_0\}$ denote the unknown parameters to be estimated.

We can use the same logic presented for the verbal stimuli to develop a state-space model for the clicks. The only exception is we rewrite the observation equation to follow for more than one click stimulus presentation per trial. In fact, for each verbal stimulus, there are four click stimuli. Hence the observation model for the clicks is:

$$Pr(m_k, n_k | p_k, q_k, 4) = p_k^{m_k}(1-p_k)^{4-m_k} \times \binom{m_k}{n_k} q_k^{n_k}(1-q_k)^{m_k-n_k}. \quad \text{Eqn. 22}$$

Where $m_k=0,1,2,3,4$ is the number of responses and $n_k=0,1,2,\ldots m_k$ is the number of correct responses to the click stimuli, otherwise $p_k, q_k, x_k$ and $z_k$ are defined exactly as they were defined for the verbal state-space model. These are six possible outcomes in any click trial block. The unknown parameters are again $\theta=\{\sigma_\varepsilon^2, \sigma_n^2, x_0, z_0\}$. Using both verbal and click stimuli allow us to determine the relevance of stimulus saliency in defining loss and recovery of consciousness.

Our objective is to develop a Bayesian procedure for state and model parameter estimation. We assume that there is a 2-dimensional state-space model for the verbal responses and a separate 2-dimensional state-space model for the verbal responses and a separate 2-dimensional state-space model for the click stimuli. We denote the unobserved state as $X=(x_{v,1}, \ldots, x_{v,K}, z_{v,1}, \ldots, z_{v,K}, x_{c,1}, \ldots, x_{c,K}, z_{c,1}, \ldots, z_{c,K})$, the model parameters as $\Theta=(\theta_v, \theta_c)$ and the observed data as $M=(m_{v,1}, \ldots, m_{v,K}, n_{v,1}, \ldots, n_{v,K}, m_{c,1}, \ldots, m_{c,K}, n_{c,1}, \ldots, n_c, K)$, where the subscripts v and c have been added to denote the verbal and click components of the model respectively. If we assume that $f(\theta)$ is a prior distribution for $(\theta)$, then by Bayes' rule the posterior distribution for the parameters and the state is:

$$f(X, \Theta | M) = \frac{f(M | X, \Theta) f(X | \Theta) f(\Theta)}{f(M)}. \quad \text{Eqn. 23.}$$

The observation models (Eqs. 17-19, 22) define $f(M|X,\Theta)$ and the state-space models (Eqs. 20-21) define $f(X|\Theta)$ and $f(M)$ is the normalizing constant. To specify $f(\Theta)$ we chose the independent prior distributions for $x_{v,0}$, $z_{v,0}$, $x_{c,0}$ and $z_{c0}$ to be uniform distributions each on the interval [0,100]. For each of the variance parameters $\sigma_{\varepsilon,v}^2$, $z_{v,0}$, $x_{c,0}$ and $\sigma_{n,c}^2$ we take as the prior distribution independent inverse gamma distributions with parameters $\alpha=5$ and $\lambda=1$.

We need the WinBUGS software to compute by Bayesian Monte Carlo methods the posterior densities $f(X,\Theta|M)$ and the marginal posterior densities of the form:

$$f(x_{c,k|M})=\iint_\Theta f(X,\Theta|M)d\Theta dX_{[c,k]}. \quad \text{Eqn. 24;}$$

where the inner integral is over the components of all values of $\Theta$ and the outer integral is over all components of X excluding $x_{c,k}$. We computed the comparable marginal posterior densities for $z_{c,k}, x_{v,k}, z_{v,k}$ and for each component of $\Theta$. We report the median of each marginal posterior density as the estimate of a given state at a particular trial and a given parameter. We report that the uncertainty in any state or parameter estimate as the 95% or 90% credibility interval based on the Monte Carlo samples. The posterior densities were computed using 100,000 iterations after a 20,000 iteration burn-in period. A Bayesian analysis implementation such as described in A. C. Smith, S Wirth, W. A. Suzuki and E. N. Brown, Bayesian analysis of interleaved learning and response bias in behavioral experiments," Journal of Neurophysiology, vol 97, pp. 2516-2524, and incorporated herein by reference, can be utilized.

The set of free parameters includes all the $x_0$ and all the $\sigma^2$. These are computed using the Bayesian approach, which assumes that prior information about the parameters improves the parameter estimates. For all the $x_0$, uniform prior distribution, uniform (a, b), can be chosen. For all the $\sigma^2$, the conjugate inverse gamma prior distribution, inverse gamma $(\alpha,\lambda)$ can be chosen. Assuming values of 0 and 100 for a and b respectively to reflect the fact that the patient's behavior markers correlates perfectly at the beginning of tracking, $\alpha$ and $\lambda$ can be chosen to be 5 and 1, making the inverse gamma prior distribution non-informative. A Bayesian analysis implementation, such as described in A. C. Smith, S. Wirth, W. A. Suzuki, and E. N. Brown, "Bayesian analysis of interleaved learning and response bias in behav-ioral experiments," Journal of Neurophysiology, vol. 97, pp. 2516-2524, 2007, and incorporated herein by reference, can be utilized.

The result is a report that can be coupled with a precise statistical characterization of behavioral dynamics. That is, behavioral dynamics, such as the points of loss-of-consciousness and recovery-of-consciousness (or other selected states) can be precisely, and statistically calculated and indicated in accordance with the present invention. Specifically, this report can aid clinicians by allowing information that was previously unknown or incapable of being discerned from traditional monitoring systems to be identified and communicated and/or used by the clinician and/or monitoring system to identify particular states of a given patient. The report may serve as part of a "human in-the-loop" operational strategy, whereby the above-described systems automatically detects spectral features of interest and the report serves as a mechanism by which to highlight or communicate the spectral features and the information extrapolated therefrom to inform clinicians of a given or predicted future state and the reasoning therebehind. Also, the report may include topographic maps of the patient's scalp or source localization maps on a brain image rendering to provide information relating to the location within the brain from which the EEG activity is being received.

For example, FIGS. 9A-9F show two sets of time domain EEG waveforms and associated spectrograms acquired during clinical use of Propofol. Specifically, a first set 900 illustrates two time domain EEG waveforms, a first EEG waveform demonstrating delta oscillation 902 (FIG. 9B) and the second EEG waveform demonstrating delta-alpha oscillation 904 (FIG. 9C). While simultaneously reading and interpreting the separate EEG waveforms 902, 904, particularly, when associated with numerous other waveforms is extremely cumbersome, an associated spectrogram 906 (FIG. 9A) displays the same delta oscillation and delta-alpha oscillation, but in form that is able to be more readily interpreted, particularly in real time. Similarly, a second set 908 illustrates two time domain EEG waveforms, a first EEG waveform demonstrating delta-alpha oscillation 910 (FIG. 9E) and the second EEG waveform demonstrating burst suppression 912 (FIG. 9F). While simultaneously reading and interpreting the separate EEG waveforms 910, 912 is difficult, an associated spectrogram 914 (FIG. 9D) displays the same delta-alpha oscillation and burst suppression, but in form that is able to be more readily interpreted in real time.

EXAMPLES

Accordingly, using the present invention, a substantial amount of new and important signatures that were previously difficult to consider or understand and/or were previously unknown or not understood as reliable without considering drug and/or patient-specific signature information, can be reliably determined and used to track a current state of a patient. For example, in the unconscious state, sevoflurane shows increased slow, delta, theta, and alpha power. Compared to propofol, the increase in theta power is pronounced and visible in the power spectrum. Slow oscillation phase-amplitude coupling shows that high frequency activity is greatest on the rising phase $(-\pi/2)$ of the slow oscillation. When ketamine is administered, power in beta and gamma bands increase. When it is administered alongside propofol, the two drugs act on the EEG in an antagonistic fashion. If enough ketamine is administered, it reduces or abolishes both slow and alpha power, and increases gamma power. Dexmedetomidine shows increased slow, delta, and sigma (12-16 Hz) power at lower doses consistent with sedation. At higher doses the EEG is dominated by slow oscillations.

The above-referenced report, as an example with respect to propofol, can indicate, predict, and/or track onset of loss of consciousness and recovery of consciousness based on increased gamma (25 to 40 Hz) and beta (12 to 25 Hz) activity; transition to unconsciousness and in the unconscious state, and recovery of consciousness based on increased/decreased slow (0 to 1 Hz), delta (1 to 4 Hz), theta (4 to 8 Hz), and alpha (8 to 12 Hz) activity; anesthetic drug administration and loss of consciousness/recovery of consciousness based on reduced theta (4 to 8 Hz) power; loss of consciousness and recovery of consciousness associated with changes in the ratio of alpha and delta (1 to 4 Hz) power in the occipital region of the scalp; states of profound unconsciousness by identifying strong global coherence in the alpha band; states of profound anesthesia based on strong association between global coherence and the state of anteriorization; profound unconsciousness based on strong modulation of the theta (4 to 8 Hz), alpha (8 to 12 Hz), beta (12 to 25 Hz), and gamma (25 to 40 Hz) activity by phase of slow and delta oscillations; transition to unconsciousness based on trough-max relationship between phase of slow oscillation and amplitude of alpha rhythm, where alpha amplitude is highest at the troughs (phase=+/−π) of the slow oscillation; profound unconsciousness based on peak-max relationship between phase of slow oscillation and amplitude of alpha rhythm, where alpha amplitude is highest at the peaks (phase=0) of the slow oscillation; and profound states of loss of consciousness based on distinct behavior in the slow oscillation (0.1 to 1 Hz) compared with the delta band (1 to 4 Hz). Of course, many and different metrics, indicators, and signatures can be identified, tracked, and used to determine a patient's state and/or predict a future patient's state.

As mentioned above, "spectral templates" for each of a plurality of exemplary drugs can be provided and used in accordance with the present invention. Specifically, to create the following "spectral templates," EEG data was acquired from operating room surgical cases during the administration of anesthesia. The data was separated into three age demographics: young (>35), middle-aged (36-59), and elderly (<60); and by drug: propofol, sevoflurane, isoflurane, dexmedetomidine, and ketamine. Spectrograms from each of the cases were analyzed to identify temporal intervals containing recurring spectral motifs correlated with putative unconscious and deep levels of anesthesia. These intervals were used to compute median spectra for each of the drug/demographic pairings.

The following relates the results of this analysis. For each of the reported median power spectra from the drug/demographic pairings, the prominent spectral peaks were identified. For each set of spectral peaks, the peak frequency, peak power, and bandwidth were estimated as a function of putative unconscious (darker) and deep (lighter) states of anesthesia. Summary schematics of the state/demographic dynamics were generated along with tables relating the defining features of each spectral peak, Referring to FIG. 10, propofol has studied. The spectral motifs for propofol included three salient spectral peaks: a low frequency (<1 Hz) oscillation, a traveling peak (spanning gamma through alpha), and a broadband gamma.

Overall dynamics during the transition from putative unconscious to deep states of anesthesia include:
Low Frequency Oscillation:
The peak frequency remains roughly constant. In some instances, a slight decrease in peak frequency may be seen.
The peak power increases.
The bandwidth remains roughly constant.
Traveling Peak:
The peak frequency decreases.
The peak power decreases.
The bandwidth remains roughly constant.
Gamma:
Broadband gamma with no clear spectral peak.
The power decreases The effect of increasing age on the spectral motif dynamics during the transition from putative unconscious to deep states of anesthesia:
Low Frequency Oscillation:
Peak frequency and bandwidth remain roughly unchanged.
The power of both unconscious and deep peaks are reduced and the difference between them increased with age.
Traveling Peak:
The peak frequency, power, and bandwidths of both unconscious and deep peaks are reduced with age.
Gamma:
The power of the broadband peaks is reduced such that there is no difference in power between them at ~40 Hz, FIG. 11 provides information similar to that of FIG. 10, in this case, with respect to sevoflurane. The spectral motifs for sevoflurane included two salient spectral peaks: a broad low frequency oscillation (spanning <1 Hz, delta, and theta bands), and a traveling peak.

Overall dynamics during the transition from putative unconscious to deep states of anesthesia:
Broad Low Frequency Oscillation:
The peak frequency remains roughly constant.
The peak power increases.
The bandwidth decreases slightly.
Traveling Peak:
The peak frequency, power, and bandwidths decrease.

The effect of increasing age on the spectral motif dynamics during the transition from putative unconscious to deep states of anesthesia:
Broad Low Frequency Oscillation:
Peak frequency is roughly unchanged.
The bandwidth is slightly reduced.
The power of both unconscious and deep peaks are reduced, and the difference between is significantly reduced such that they have the same power across unconscious and deep states.
Traveling Peak:
The peak frequency, power, and bandwidth of both unconscious and deep peaks are reduced, and the differences between their values are increased.

Figure 10:
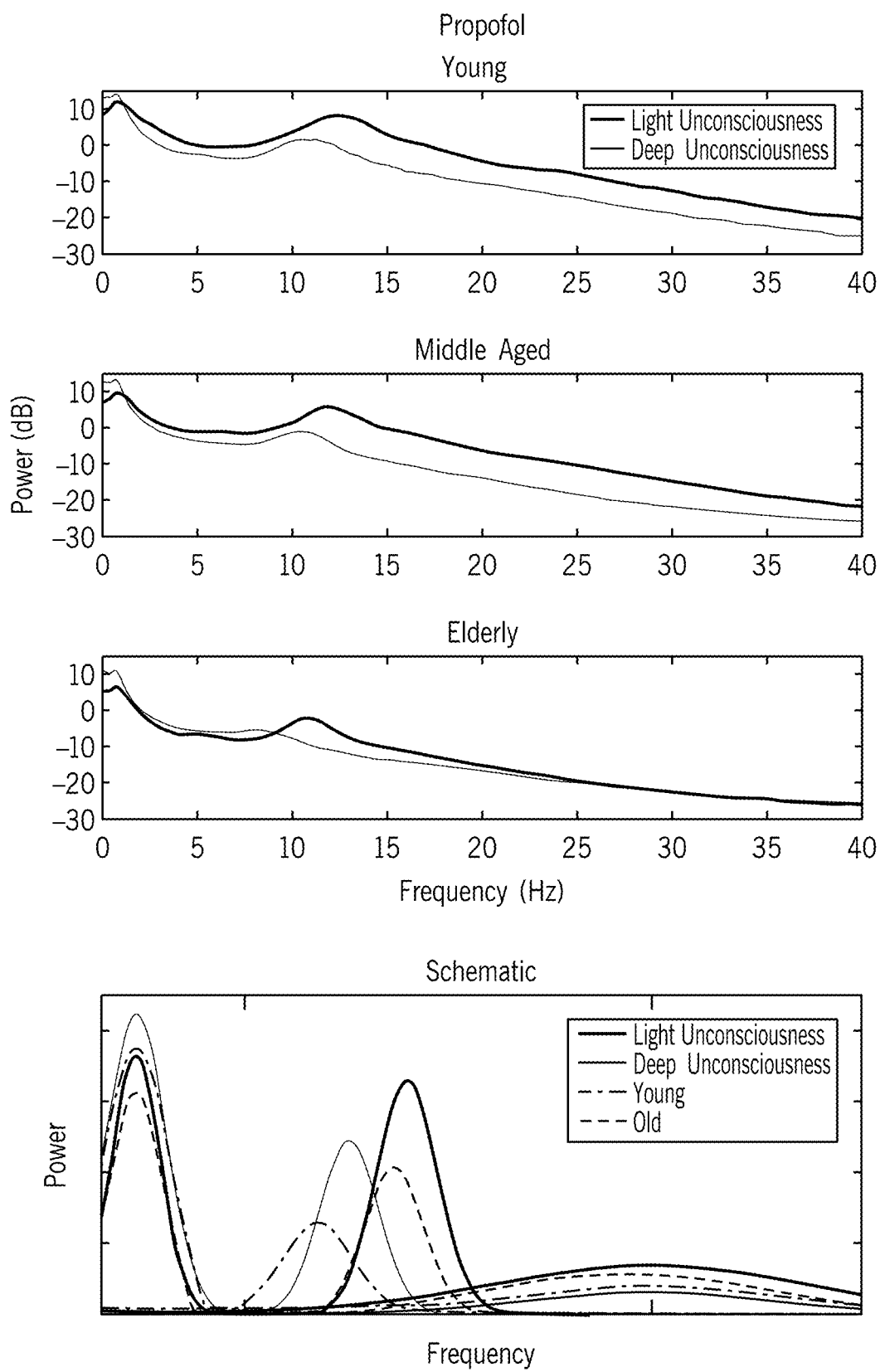
FIGS. 10-15 are graphs, each figure corresponding to a different drug, that illustrate the ability to create "spectral templates" for each of a plurality of exemplary drugs, which can be used in accordance with the present invention.
Figure 11:
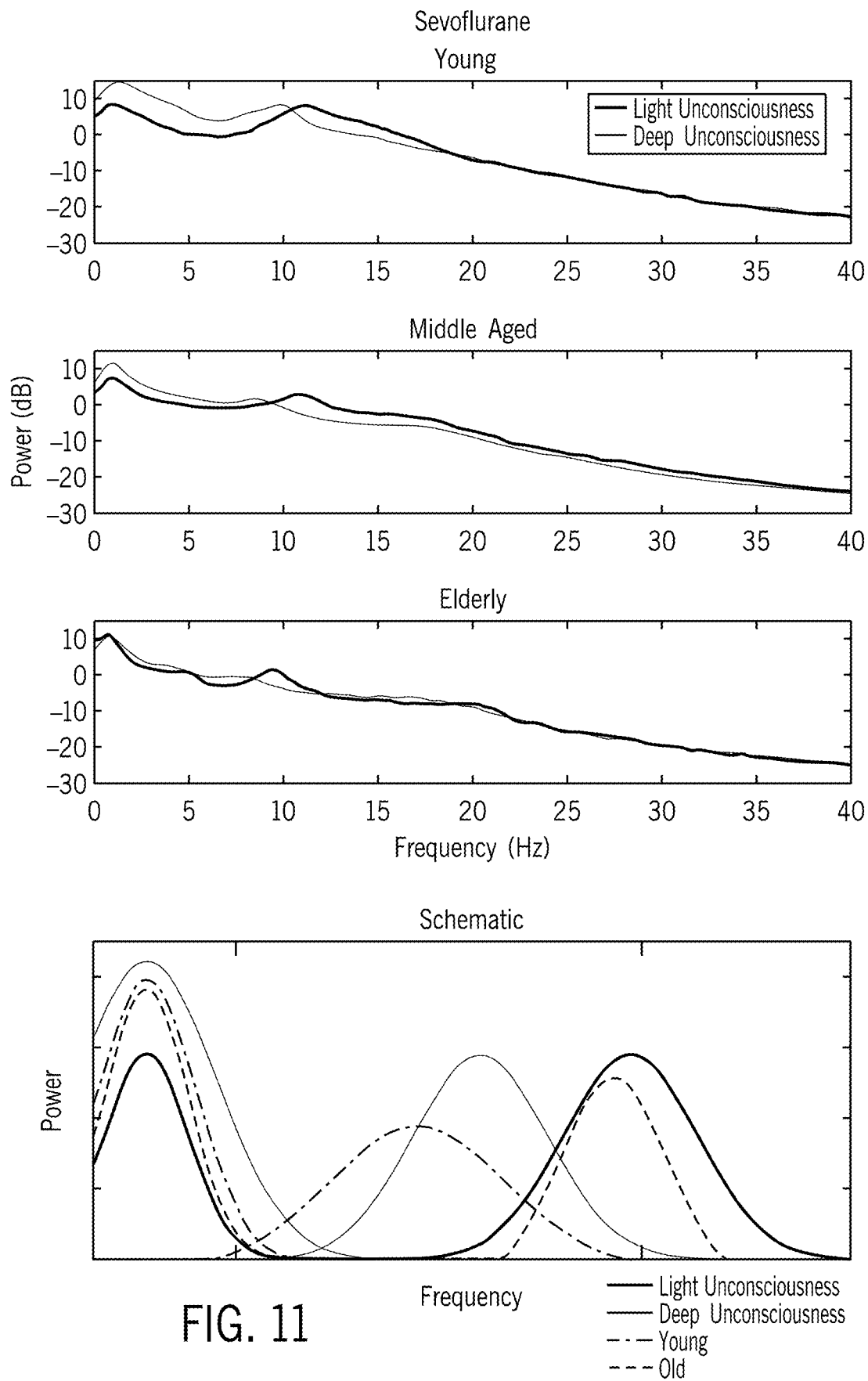
Figure 12:
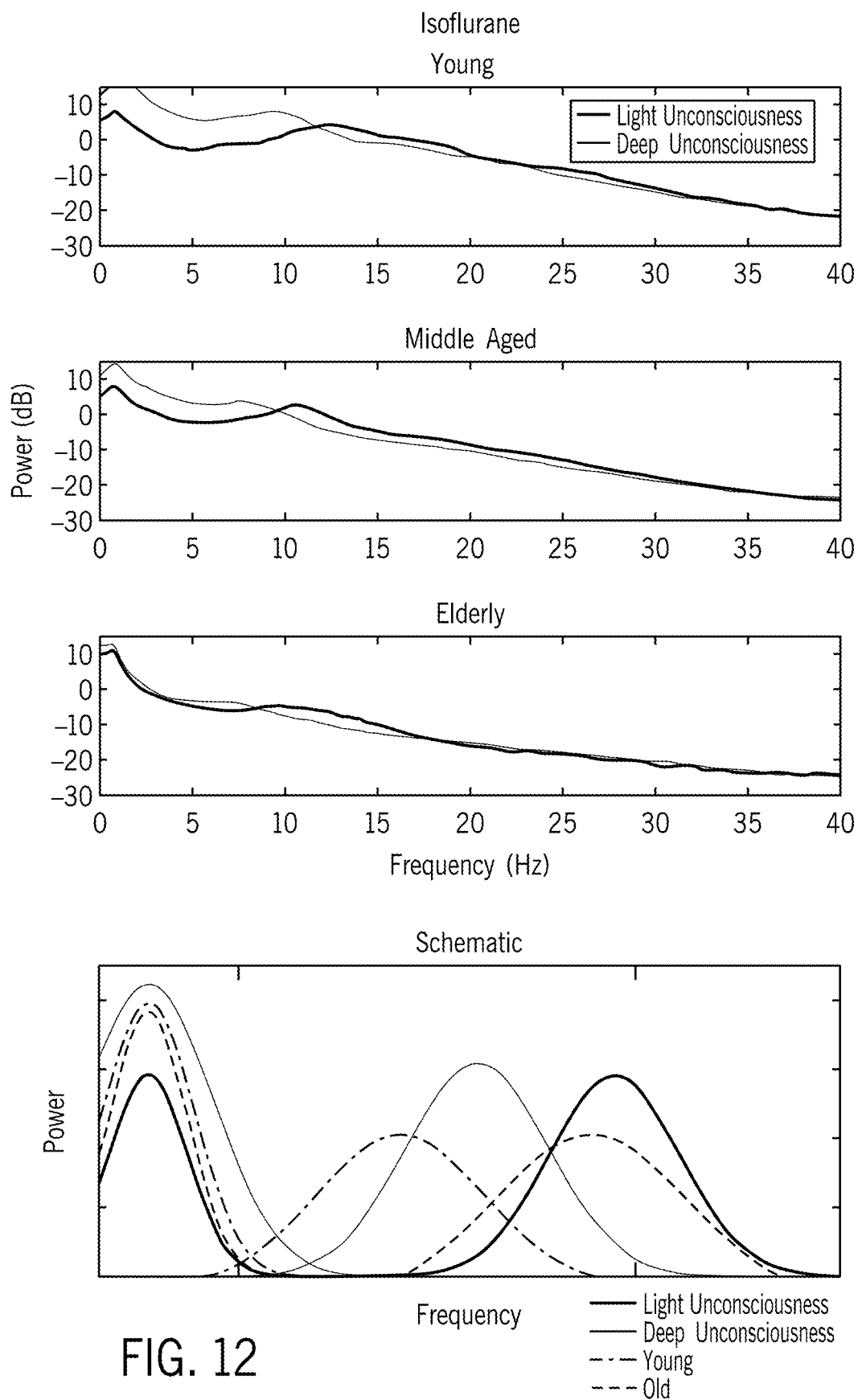

FIG. 12 provides information similar to that of FIGS. 10 and 11, in this case, with respect to isoflurane. The spectral motifs for isoflurane included two salient spectral peaks: a broad low frequency oscillation (spanning <1 Hz, delta and theta bands), and a traveling peak.

Overall dynamics during the transition from putative unconscious to deep states of anesthesia:
Broad Low Frequency Oscillation:
The peak frequency remains roughly constant.
The peak power increases.
The bandwidth decreases slightly.
Traveling Peak:
The peak frequency, power, and bandwidths decrease.
The effect of increasing age on the spectral motif dynamics during the transition from putative unconscious to deep states of anesthesia:
Broad Low Oscillation:
Peak frequency is roughly unchanged.
The bandwidth is slightly reduced.
The power of both unconscious and deep peaks are reduced, and the difference between is significantly reduced such that they have the same power across unconscious and deep states.
Traveling Peak:
The peak frequency is reduced, and the differences between their values are increased.
The power of both unconscious and deep peaks are reduced, and the difference between is significantly reduced such that they have the same power across unconscious and deep states.
The bandwidth is slightly reduced.

Figure 13:
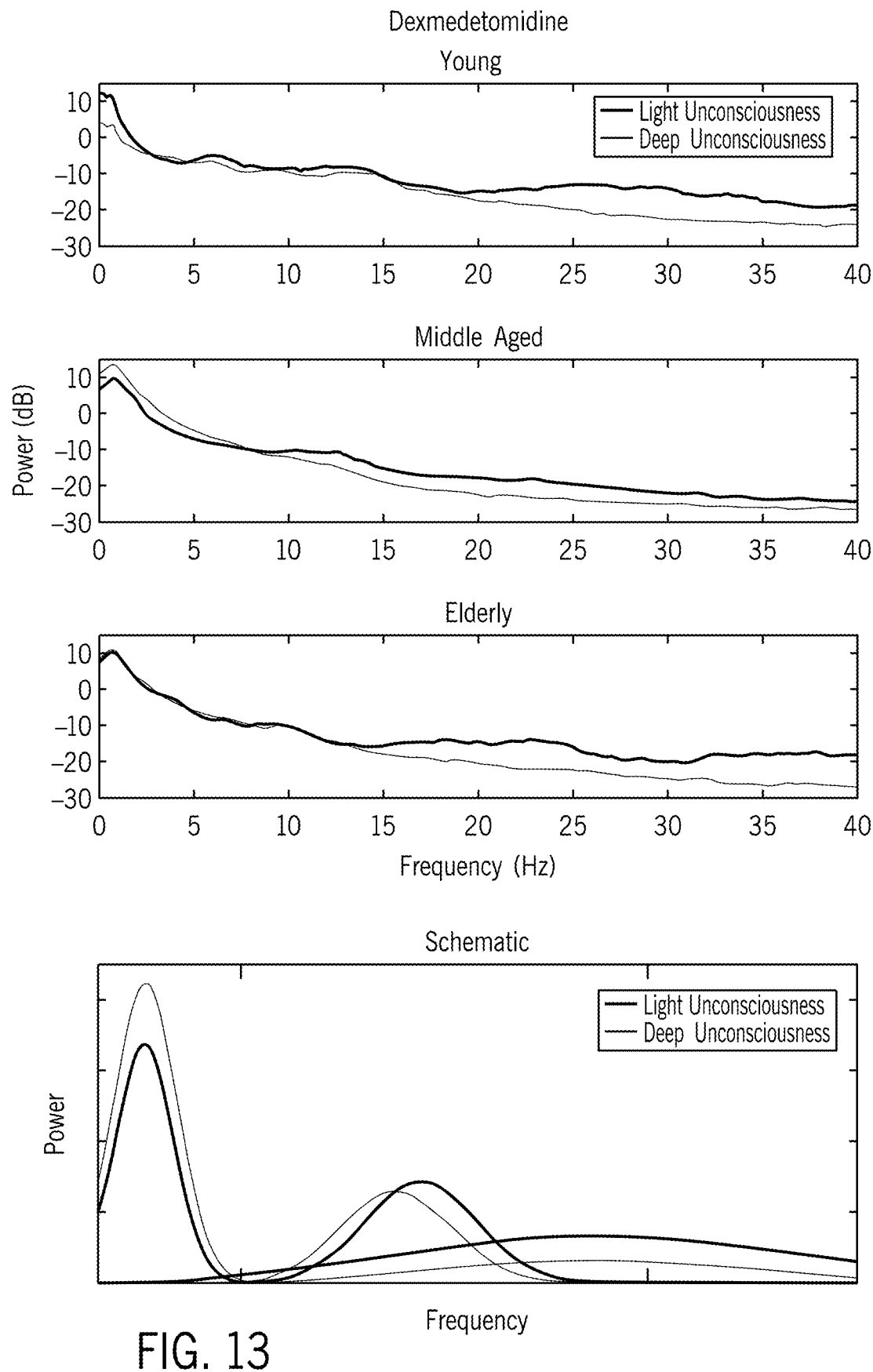

FIG. 13 provides information similar to that of FIGS. 10-12, in this case, with respect to dexmedetomidine. The data for young and elderly patients were limited and showed spectral heterogeneity. Thus, we report only the findings for the middle aged demographic. With respect to identified peaks, the spectral motifs for dexmedetomidine included three salient spectral peaks: low frequency oscillation, a non-stationary "spindle" peak spanning alpha and sigma bands, and broadband gamma.

Overall dynamics during the transition from putative unconscious to deep states of anesthesia:
Slow Oscillation:
The peak frequency remains roughly constant.
The peak power increases.
The bandwidth remains roughly constant.
Spindle Peak:
The peak frequency decreases though remains in high alpha/low sigma (spindle) range.
The peak power decreases.
The bandwidth remains roughly constant.
Gamma:
Broadband gamma with no clear spectral peak.
The power decreases.

Figure 14:
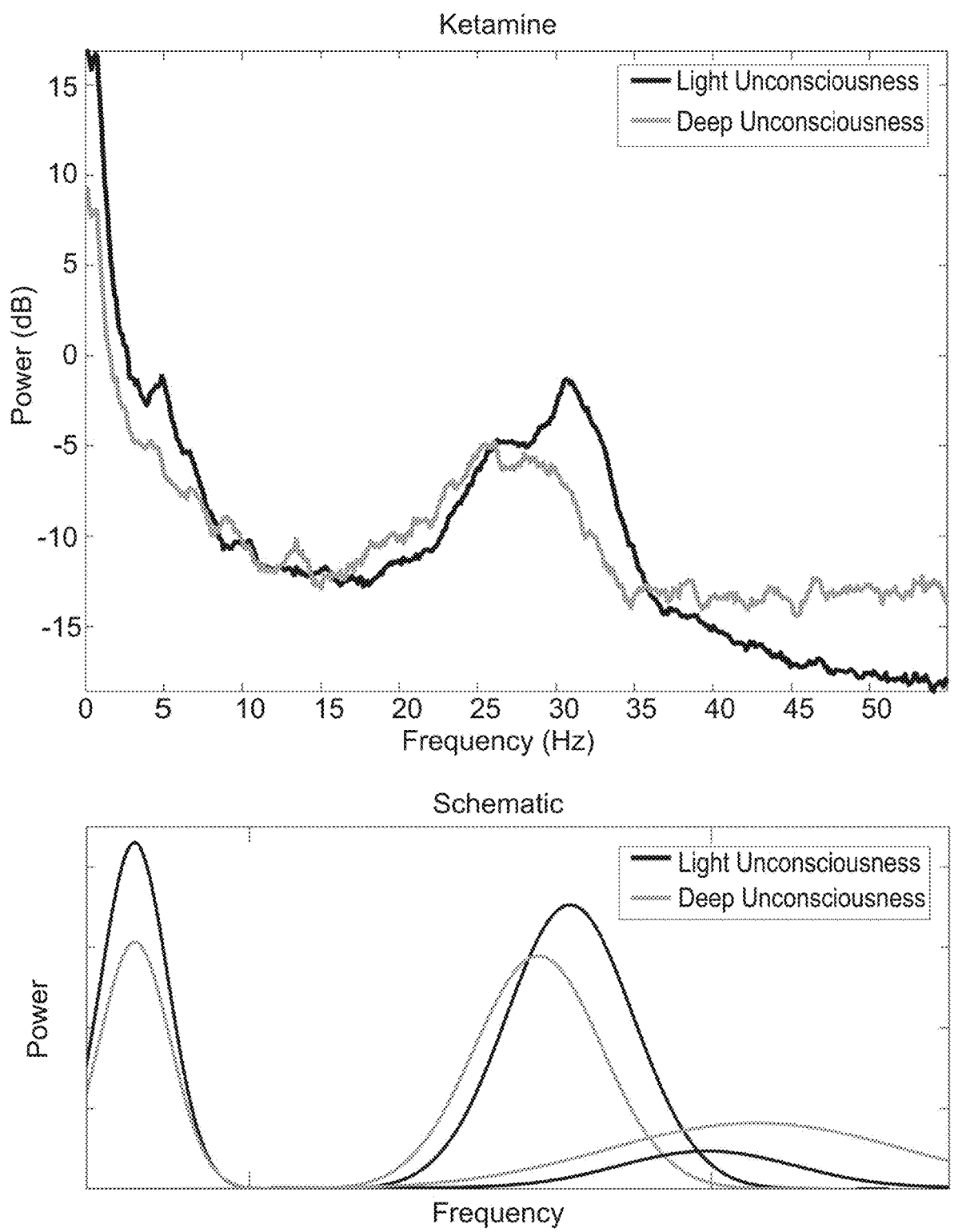

FIG. 14 provides information similar to that of FIGS. 10-13, in this case, with respect to ketamine. Data was acquired from one middle aged patient. The effects, however, seem marked between putative unconscious and deep states of anesthesia. With respect to identified peaks, the spectral motifs for ketamine included three salient spectral peaks: the low frequency oscillation, and a non-stationary low gamma peak, and broadband high gamma (up to 150 Hz). Overall dynamics during the transition from putative unconscious to deep states of anesthesia:
Low Frequency Oscillation:
The peak frequency remains roughly constant.
The peak power decreases.
The bandwidth remains roughly constant.
Low Gamma Peak:
The peak frequency and power decrease.
The bandwidth remains roughly constant.
High Gamma:
Broadband gamma with no clear spectral peak.
The power increases.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

For example, the present invention has ready use and clinical need in fields of medicine other than anesthesiology. For example, other medical specialties either use or have interest in the use of drugs such as those described above and other similar drugs. The above-described systems and methods are useful for managing drugs in a wide variety of situations. For example, the present invention can be used during pharmacological therapies to induce and maintain sedation. Also, the present invention can be particularly useful in the intensive care unit where intense therapies are administered and clinicians can benefit from additional monitoring and feedback. Further still, the present invention can be of use in outpatient settings, including outpatient treatments involving pharmacologically-induced sleep, involving sedation, for example, using dexmedetomidine. Also, the present invention can be used in psychiatry settings to aid in the treatment of depression with ketamine, for example. These are but a few of the wide-variety of clinical and non-clinical settings where the present invention can be readily applied.

The invention claimed is:

1. A system for monitoring a patient experiencing an administration of at least one drug having anesthetic properties, the system comprising:
   a monitoring device comprising sensors configured to acquire electroencephalogram (EEG) signals from the patient;
   a monitoring system, in communication with the monitoring device, that comprises:
      a user interface configured to receive a selection from a user indicating at least one patient characteristic including at least an age of the patient and at least one drug administered to the patient, and wherein the at least one drug is one of a plurality of drugs each having at least one corresponding template;
      at least one processor configured to:
         assemble the EEG signals acquired using the sensors into sets of time-series data using local referencing;
         transform each set of locally referenced time-series data into spectrum information characterizing spectral power in at least one frequency band, and into phase-amplitude information characterizing a relationship between an amplitude of a first selected frequency band and a phase of a second selected frequency band;
         analyze the spectrum information and phase-amplitude information using at least one templates corresponding to the at least one patient characteristic that includes at least the age of the patient and the at least one drug administered to the patient indicated by the selection;
         determine at least a predicted future state of the patient based on the analysis; and
         generate a report identifying at least one predicted future state of the patient induced by the at least one drug; and
      a display for providing the report to the user.

2. The system of claim 1, wherein the report indicates spatiotemporal activity at different states of the patient receiving the at least one drug.

3. The system of claim 1, wherein the at least one processor is further configured to analyze an amplitude envelope of activity in at least one of the sets of time-series data to identify a maxima at a selected frequency based on a phase of a lower frequency rhythm.

4. The system of claim 1, wherein the at least one processor is further configured to perform a modulogram analysis to measure a phase-amplitude coupling in a time-resolved fashion to identify modes of phase-amplitude coupling corresponding to at least the predicted future state of the patient receiving the at least one drug.

5. The system of claim 4, wherein the at least one processor is further configured to determine at least one of a spatial and a local average of data acquired by several of the sensors to perform the modulogram analysis.

6. The system of claim 1, wherein the selection indicates at least one of a drug selected from the list consisting essentially of Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifentanil, Fentanyl, Sufentanil, Alfentanil, and drug administration information comprising at least one of drug timing, drug dose, and drug administration rate.

7. The system of claim 1, wherein the at least one processor is further configured to implement a dynamic Bayesian processing method to characterize the patient as exhibiting a predetermined behavioral dynamic based on the spectrum information and global coherence information.

8. The system of claim 7, wherein the predetermined behavioral dynamic comprises at least one of a loss consciousness and recovery of consciousness.

9. The system of claim 1, wherein the monitoring device further comprises at least one of heart rate monitors, blood pressure monitors, and sensors configured to monitor galvanic skin response (GSR).

10. A system for monitoring a patient experiencing an administration of at least one drug having anesthetic properties, the system comprising:
 a monitoring device comprising a plurality of sensors configured to acquire electroencephalogram (EEG) signals from the patient;
 a user interface configured to receive a selection from a user indicating at least one patient characteristic that at least includes an age of the patient and the at least one drug administered to the patient, wherein the at least one drug is one of a plurality of drugs each having at least one corresponding spectral template;
 at least one processor, in communication with the monitoring device, that is configured to:
  assemble sets of time-series data using the EEG signals, wherein each set of time-series data corresponds to EEG signals recorded at a sensor location in reference to a combination of EEG signals obtained from a local neighborhood about the sensor location;
  for each sensor location, generate spectrum information characterizing spectral power in at least one selected frequency band using the corresponding set of locally referenced time-series data;
  analyze the spectrum information using at least one spectral templates corresponding to the patient characteristic that includes at least the age of the patient and the at least one drug;
  identify, based on the analysis, a state of the patient induced by the at least one drug on the patient; and
  generate a report indicating the state of the patient;
 a display for providing the report to the user.

11. The system of claim 10, wherein the at least one processor is further configured to generate global coherence information using the sets of time-series data, and analyze the global coherence information to determine state of the patient.

12. The system of claim 10, wherein the at least one processor is further configured to transform each set of time-series data into a spectrogram, and analyze the spectrogram to determine at least one of a current state and a predicted future state of the patient.

13. The system of claim 10, wherein the report indicates spatiotemporal activity at different stages when the patient receiving the at least one drug.

14. The system of claim 10, wherein the at least one processor is further configured to analyze an amplitude envelope of activity in at least one of the sets of times-series data to identify a maxima at a selected frequency based on a phase of a lower frequency rhythm.

15. The system of claim 10, wherein the at least one processor is further configured to perform a modulogram analysis to measure a phase-amplitude coupling in a time-resolved fashion to identify modes of phase-amplitude coupling corresponding to at least one of a current state and a predicted future state of the patient receiving the at least one drug.

16. The system of claim 10, wherein the selection indicates at least one of a drug selected from the list consisting essentially of Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, isoflurane, Desflurane, Remifentanil, Fentanyl, Sufentanil, Alfentanil, and drug administration information comprising at least one of drug timing, drug dose, and drug administration rate.

17. The system of claim 10, wherein the at least one processor is further configured to implement a dynamic Bayesian processing method to characterize the patient as exhibiting a predetermined behavioral dynamic.

18. The system of claim 17, wherein the predetermined behavioral dynamic comprises at least one of a loss consciousness and recovery of consciousness.

19. The system of claim 10, wherein the at least one processor is further configured to determine a probability of response to stimuli based on the analysis.

* * * * *

UNITED STATES PATENT AND TRADEMARK OFFICE
CERTIFICATE OF CORRECTION

PATENT NO. : 11,751,770 B2
APPLICATION NO. : 16/165580
DATED : September 12, 2023
INVENTOR(S) : Emery N. Brown et al.

Page 1 of 2

It is certified that error appears in the above-identified patent and that said Letters Patent is hereby corrected as shown below:

In the Specification

Column 7, Line 12, "a activity" should be --α activity--.

Column 7, Line 43, "$C_{ij}^Y(f)=C_{ij}^Y(f)\delta_{ij}$" should be -- $C_{ij}^Y(f) = C_{ij}^K(f)\delta_{ij}$ --.

Column 7, Line 52, "$\Sigma_{j=1}^N |U_{ji}(f)|^2 = 1$" should be -- $\sum_{j=1}^N |U_{ji}(f)|^2 = 1$ --.

Column 7, Line 56, "$S_1^Y(f) \geq S_2^Y(f) \geq \ldots \geq S_N^Y(f)$" should be -- $S_1^Y(f) \geq S_2^Y(f) \geq \ldots \geq S_N^Y(f)$ --.

Column 8, Line 26, "a range" should be --α range--.

Column 8, Line 37, "a range" should be --α range--.

Column 9, Lines 53-54, "$\int_{-\pi}^{\pi} M(t,\phi)d\phi = 1$" should be -- $\int_{-\pi}^{\pi} M(t,\phi)d\phi = 1$ --.

Column 11, Eq. 9, Line 53, "$A_w(t) := \sqrt{(\Sigma_{k=1}^N w_k \alpha_k(t))^2 + (\Sigma_{k=1}^N K^{\mathcal{H}} \overline{k(\alpha_k(t))})^2}$" should be -- $A_w(t) := \sqrt{\sum_{k=1}^N w_k \alpha_k(t)^2 + \left(\sum_{k=1}^N w_k \mathcal{H}_k(\alpha_k(t))\right)^2}$ --.

Column 11, Eq. 10, Line 56, "$\theta_w(t) := \arg(\Sigma_{k=1}^N w_k s_k(t) + \Sigma_{k=1}^N wK^{\mathcal{H}}(s_k(t)))$" should be -- $\theta_w(t) := \arg\left(\sum_{k=1}^N w_k s_k(t) + \sum_{k=1}^N w_k \mathcal{H}(s_k(t))\right)$ --.

Signed and Sealed this
Twenty-first Day of November, 2023

Katherine Kelly Vidal
*Director of the United States Patent and Trademark Office*

CERTIFICATE OF CORRECTION (continued)
U.S. Pat. No. 11,751,770 B2

Column 12, Eq. 12, Line 4, "$A_w(\theta)\bar{\omega} + \Sigma_{k=1}^{\infty} \alpha_k \sin(k\theta) + b_k \cos(k\theta)$," should be --$A_w(\theta)\bar{\omega} + \Sigma_{k=1}^{\infty} \alpha_k \sin(k\theta) + b_k \cos(k\theta)$--.

Column 12, Line 5, "$a_k$" should be --$\alpha_k$--.

Column 12, Eq. 13, Line 13, "$R(\mu\{\alpha_k, b_k\}; w) := \int_{k=1}^{L} \{A_W(\theta) - \mu - \Sigma_{k=1}^{L}(\alpha_k \sin(k\theta) + b_k \cos(k\theta))\}^2 p(\theta)d\theta$," should be --$R(\mu\{\alpha_k, b_k\}; w) := \int_{k=1}^{L} \{A_W(\theta) - \mu - \Sigma_{k=1}^{L}(\alpha_k \sin(k\theta) + b_k \cos(k\theta))\}^2 p(\theta)d\theta$--.

Column 12, Eq. 14, Line 20, "$R(\mu\{\alpha_k, b_k\}; w) := \int_{-\pi}^{\pi} \{E_T\{A_W(t_w\theta)\}\} - \mu - \Sigma_{k=1}^{L}(\alpha_k \sin(k\theta) + b_k \cos(k\theta))\}^2 p(\theta)d\theta$" should be --$R(\mu\{\alpha_k, b_k\}; w) := \int_{-\pi}^{\pi} \{E_T\{A_W(t_w\theta)\}\} - \mu - \sum_{k=1}^{L}(\alpha_k \sin(k\theta) + b_k \cos(k\theta))\}^2 p(\theta)d\theta$--.

Column 12, Eq. 15, Line 34, "$\frac{1}{T}\sum_{t=0}^{T} \{A_w(t) - \mu - \sum_{k=1}^{L}(\alpha_k \sin(k\theta_w) + b_k \cos(k\theta_w))\}^2$" should be --$\frac{1}{T}\sum_{t=0}^{T} \{A_w(t) - \mu - \sum_{k=1}^{L}(\alpha_k \sin(k\theta_w) + b_k \cos(k\theta_w))\}^2$--.

Column 14, Line 17, "and $q_k$" should be --and let $q_k$--.

Column 14, Line 37, "$\sigma_\varepsilon^2 \Delta_k$ and $\sigma_n^2 \Delta_k$" should be --$\sigma_\varepsilon^2 \Delta_k$ and $\sigma_n^2 \Delta_k$--.

Column 14, Line 47, "$\theta = \{\sigma_\varepsilon^2, \sigma_n^2, x_0, z_0\}$" should be --$\theta = \{\sigma_\varepsilon^2, \sigma_n^2, x_0, z_0\}$--.

Column 15, Line 29, "$\sigma_{\varepsilon,v}^2$" should be --$\sigma_{\varepsilon,v}^2$--.

Column 15, Line 29, "$\sigma_{n,c}^2$" should be --$\sigma_{n,c}^2$--.

In the Claims

Column 20, Claim 1, Line 57, "templates" should be --template--.

Column 22, Claim 10, Line 6, "templates" should be --template--.